United States Patent

Heaton et al.

[11] Patent Number: 5,879,357
[45] Date of Patent: Mar. 9, 1999

[54] APPARATUS FOR MARKING TISSUE LOCATION

[75] Inventors: Lisa W. Heaton, Norwalk; Mitchell J. Palmer, New Milford; Keith L. Milliman, Bethel; Jonathan E. Wilson, Fairfield, all of Conn.

[73] Assignee: United States Surgical Corporation, Norwalk, Conn.

[21] Appl. No.: 926,695

[22] Filed: Sep. 10, 1997

Related U.S. Application Data

[63] Continuation of Ser. No. 823,889, Mar. 17, 1997, abandoned, which is a continuation of Ser. No. 546,483, Oct. 20, 1995, abandoned.

[51] Int. Cl.⁶ .................................................. A61B 17/00
[52] U.S. Cl. ............................ 606/116; 600/567; 604/95
[58] Field of Search .............................. 606/185, 159, 606/232, 213, 220, 127; 604/51, 165, 164, 905, 95; 600/434, 435, 562, 567

[56] References Cited

U.S. PATENT DOCUMENTS

| | | |
|---|---|---|
| 3,836,776 | 9/1974 | Gullekson . |
| 4,007,732 | 2/1977 | Kvayle et al. . |
| 4,230,123 | 10/1980 | Hawkins, Jr. . |
| 4,235,238 | 11/1980 | Oglio et al. . |

(List continued on next page.)

FOREIGN PATENT DOCUMENTS

| | | |
|---|---|---|
| A 481 685 A1 | 4/1992 | European Pat. Off. . |
| 2919009 | 11/1979 | Germany . |
| 4216694 | 12/1992 | Germany . |
| WO 86/05378 | 9/1986 | WIPO . |
| WO93/009720 A1 | 5/1993 | WIPO .................................. 606/185 |

OTHER PUBLICATIONS

Acufex Microsurgical, Inc. Product Brochure, 1994.
Duh et al., "New Laparoscopic Placement of Gastronomy & Jejunostomy Feeding Tubes", (Jun. 1993 4 pgs.).
Duh et al., "Laparoscopic Gastronomy Using T–fasteners as Retractors and Anchors", (1993, pp. 60–63).
C. Cope et al., "Cope Gastrointestinal Suture Anchor Sets", (1992, 4 pgs.).

*Primary Examiner*—Richard J. Apley
*Assistant Examiner*—Justine R. Yu

[57] ABSTRACT

A surgical apparatus for marking a location within tissue which includes (i) a needle including a housing and an elongated tube having a sharp distal end, (ii) an elongated cable configured and dimensioned to pass through a longitudinal passageway formed through the needle, (iii) an elongated tissue marker attached adjacent a distal end of the elongated cable such that the elongated marker is movable between a retracted orientation and a deployed orientation, and (iv) an actuator assembly operatively associated with the elongated marker, wherein movement of the actuator assembly from a first position to a second position moves the elongated marker from the retracted position to the deployed position. A method of marking a particular location in body tissue is also provided, which includes the steps of (i) inserting an apparatus into a section of body tissue, (ii) deploying an elongated marker having an elongated cable attached thereto from the apparatus into the tissue, (iii) retaining the elongated cable relative the distal end of the apparatus, and (iv) moving the elongated marker into an orientation substantially perpendicular to the elongated cable.

25 Claims, 16 Drawing Sheets

U.S. PATENT DOCUMENTS

| | | |
|---|---|---|
| 4,592,356 | 6/1986 | Gutierrez . |
| 4,669,473 | 6/1987 | Richards et al. . |
| 4,682,606 | 7/1987 | DeCaprio . |
| 4,741,330 | 5/1988 | Hayhurst ................................... 128/92 |
| 4,774,948 | 10/1988 | Markham . |
| 4,790,329 | 12/1988 | Simon ..................................... 128/754 |
| 4,799,495 | 1/1989 | Hawkins et al. . |
| 4,931,059 | 6/1990 | Markham ............................... 606/185 |
| 4,966,583 | 10/1990 | Debbas . |
| 4,986,279 | 1/1991 | O'Neill . |
| 5,011,473 | 4/1991 | Gatturna . |
| 5,021,059 | 6/1991 | Kensey et al. .......................... 606/213 |
| 5,031,634 | 7/1991 | Simon . |
| 5,041,129 | 8/1991 | Hayhurst et al. . |
| 5,059,197 | 10/1991 | Urie et al. . |
| 5,111,828 | 5/1992 | Kornberg et al. . |
| 5,123,914 | 6/1992 | Cope . |
| 5,127,916 | 7/1992 | Spencer et al. . |
| 5,158,084 | 10/1992 | Ghiatas . |
| 5,158,565 | 10/1992 | Marcadis et al. . |
| 5,195,540 | 3/1993 | Shiber . |
| 5,197,482 | 3/1993 | Rank et al. . |
| 5,197,484 | 3/1993 | Kornberg et al. . |
| 5,213,575 | 5/1993 | Scotti ........................................ 604/95 |
| 5,217,453 | 6/1993 | Kring ..................................... 128/772 |
| 5,221,269 | 6/1993 | Miller et al. . |
| 5,234,426 | 8/1993 | Rank et al. . |
| 5,269,809 | 12/1993 | Hayhurst et al. ...................... 606/220 |
| 5,301,682 | 4/1994 | Debbas . |
| 5,353,804 | 10/1994 | Kornberg et al. ...................... 128/754 |
| 5,409,004 | 4/1995 | Sloan ..................................... 604/164 |
| 5,417,691 | 5/1995 | Hayhurst . |
| 5,445,645 | 8/1995 | Debbas . |
| 5,488,958 | 2/1996 | Topel et al. . |

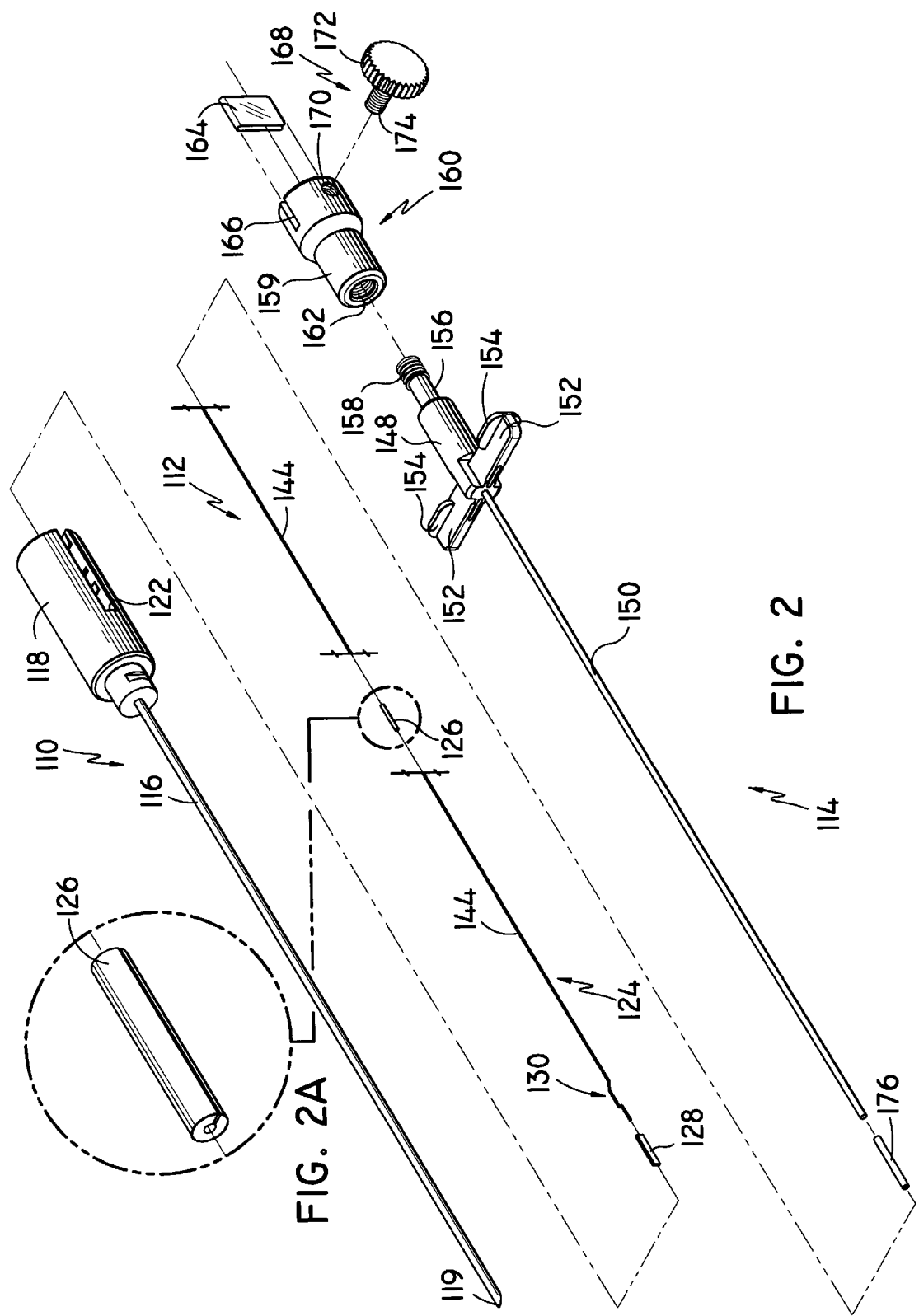

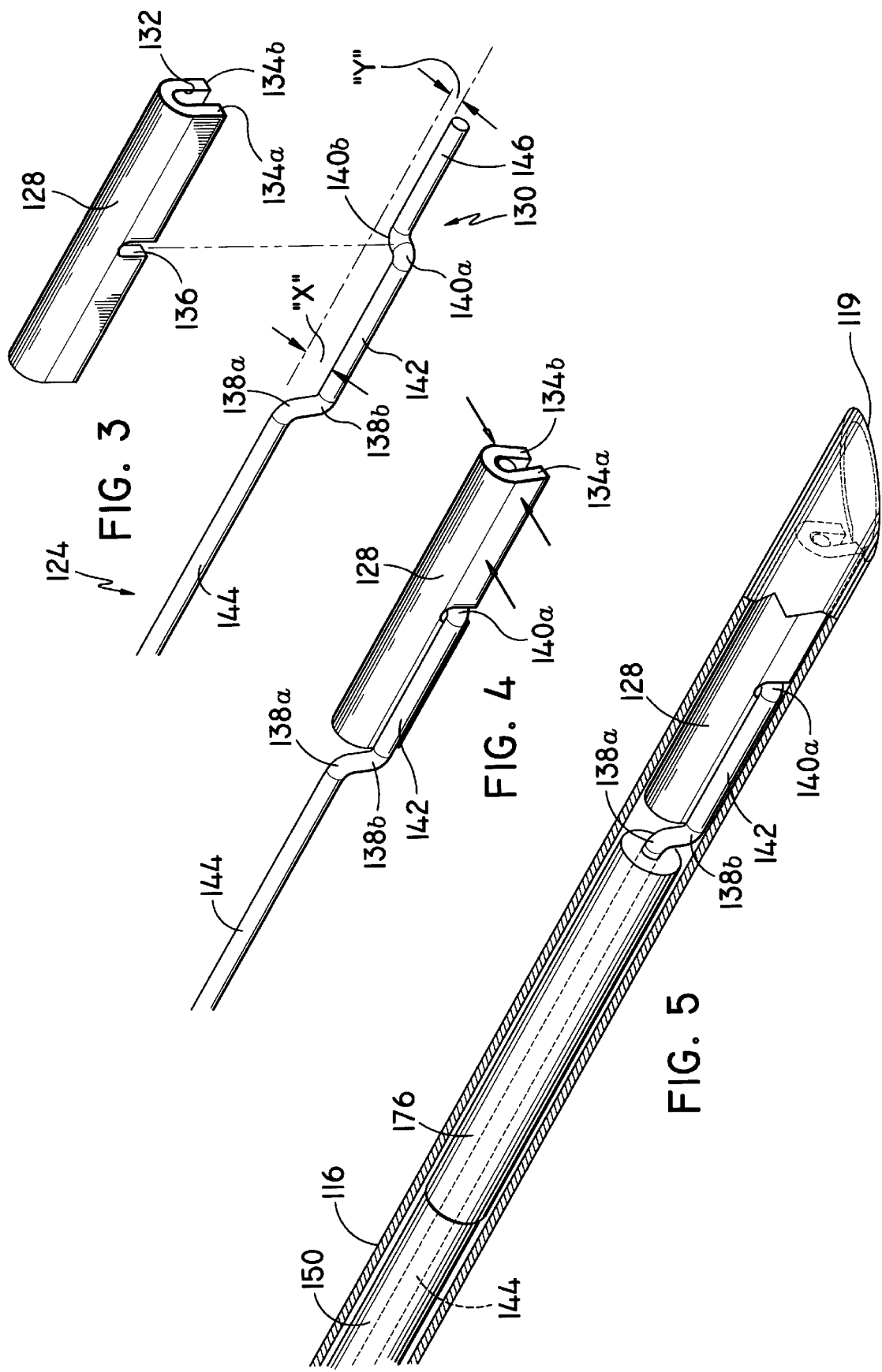

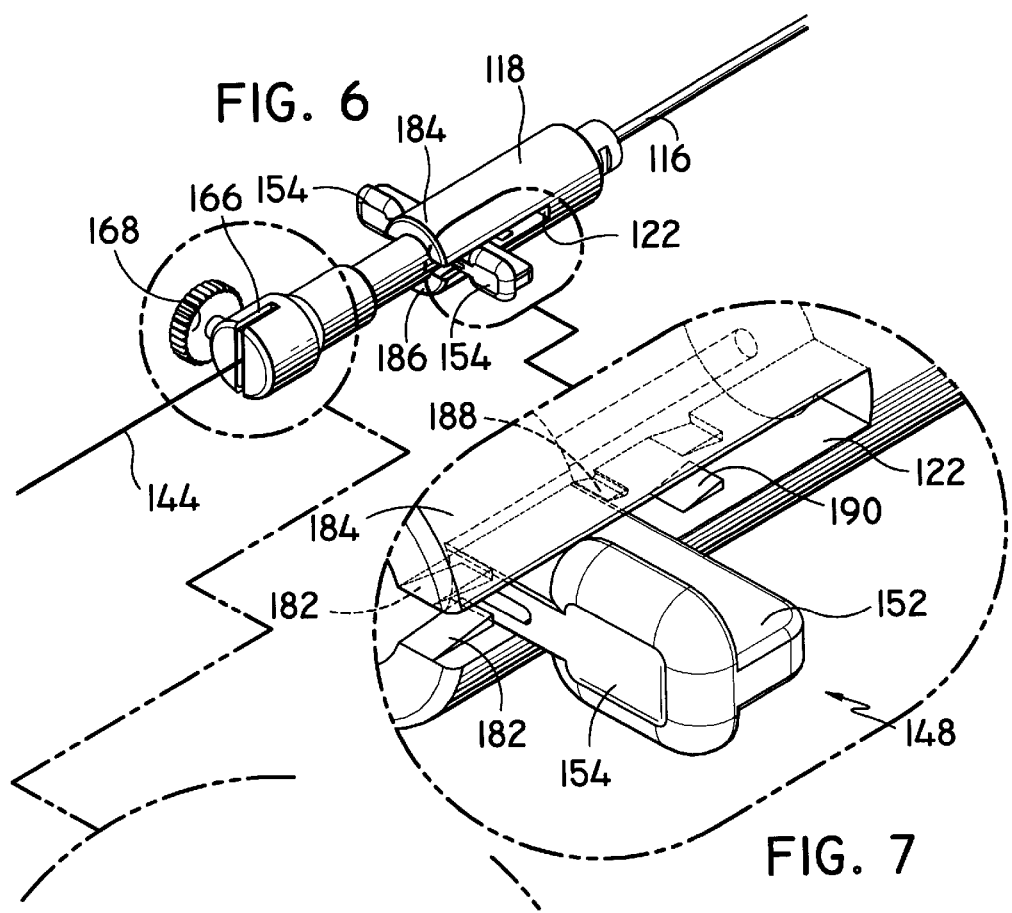
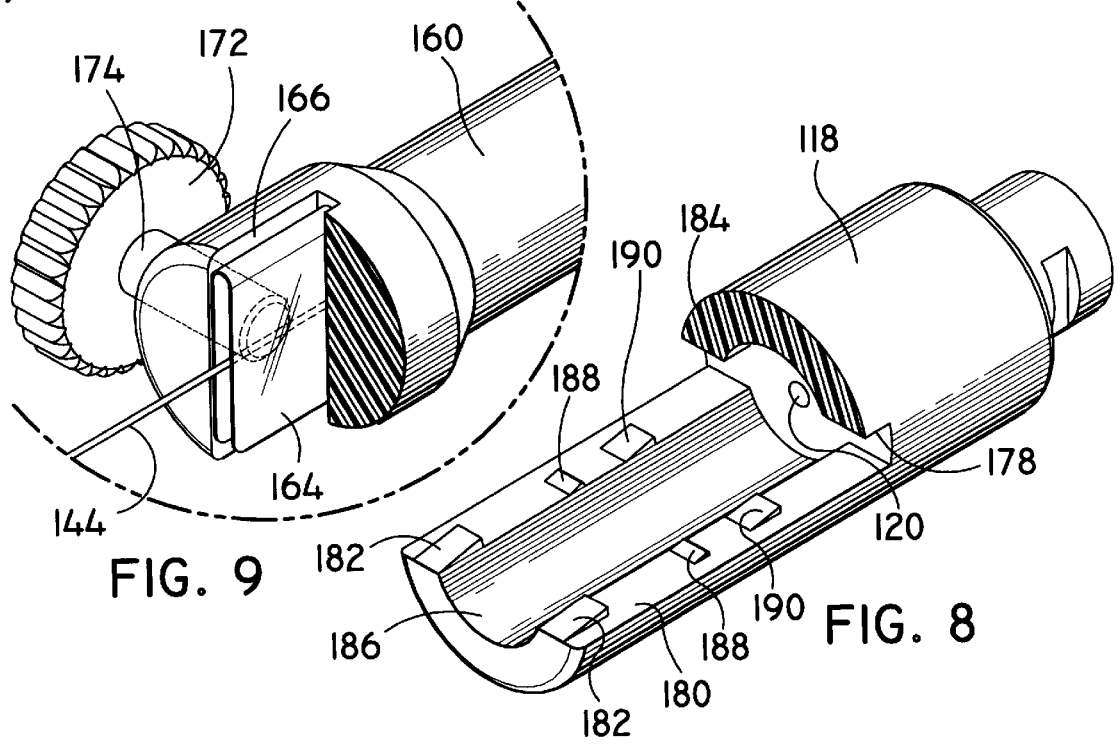

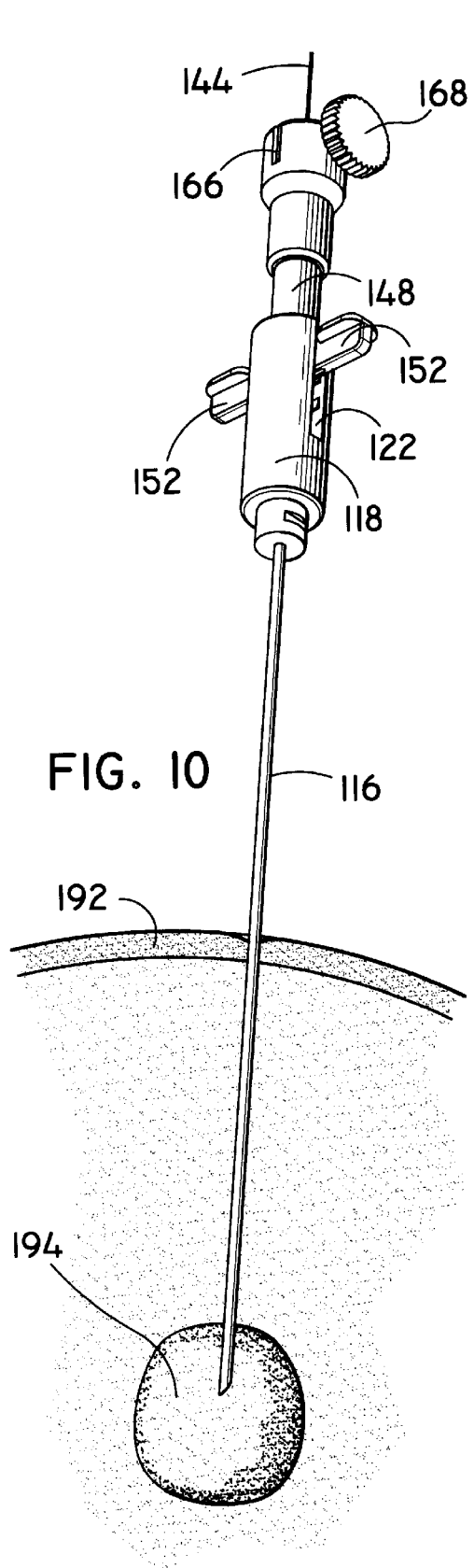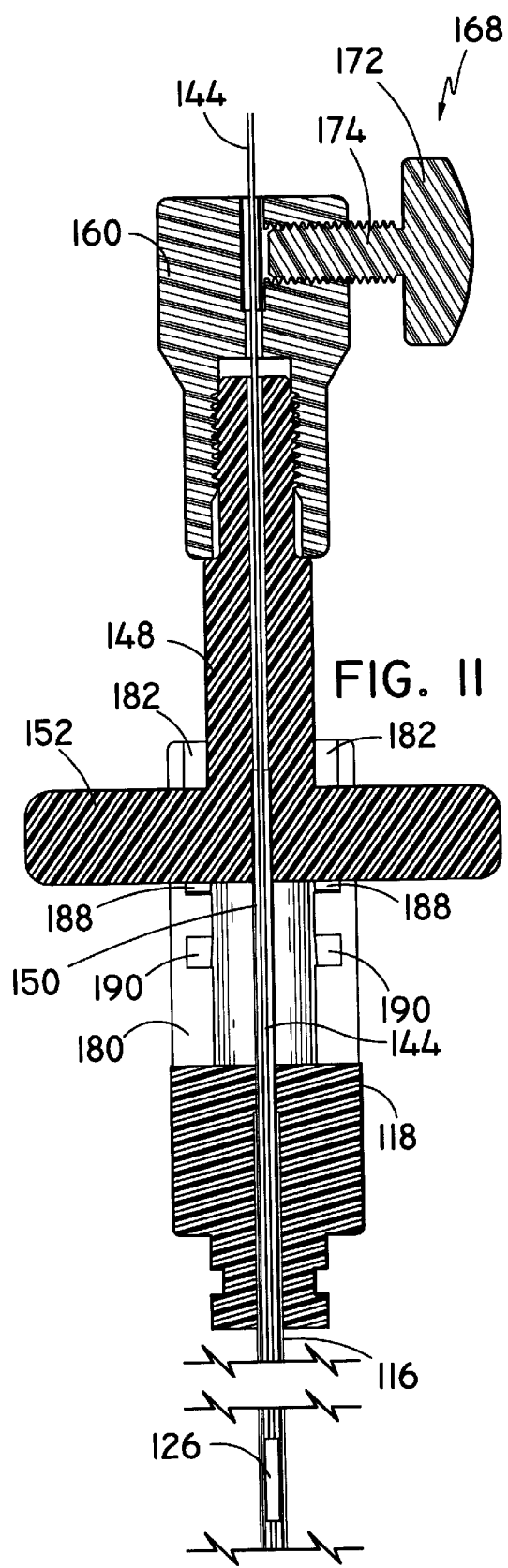

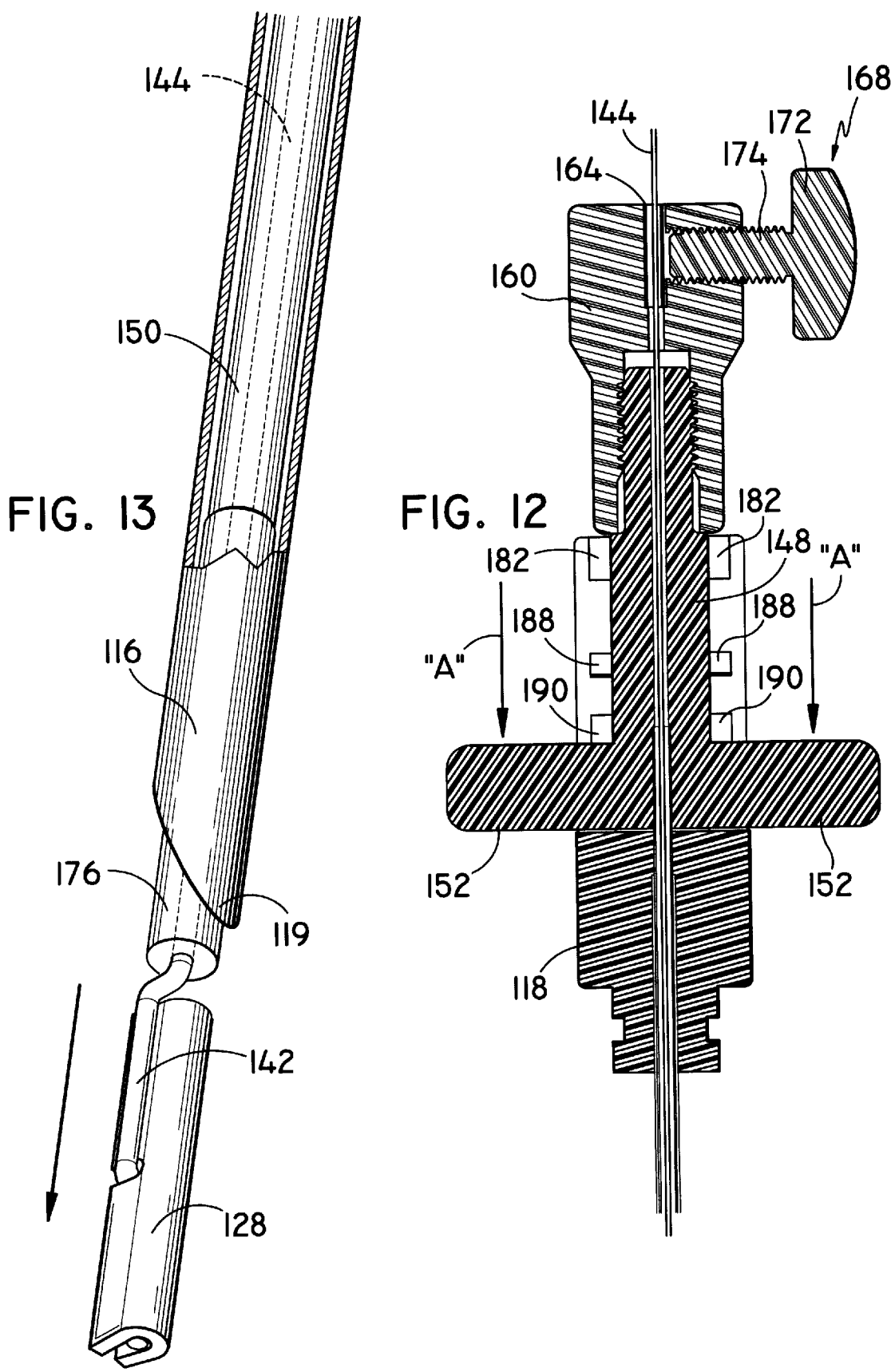

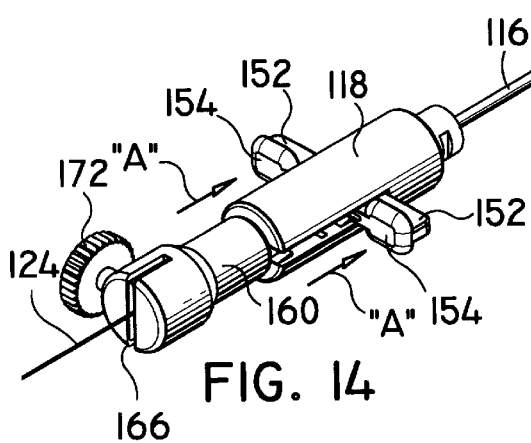
FIG. 14
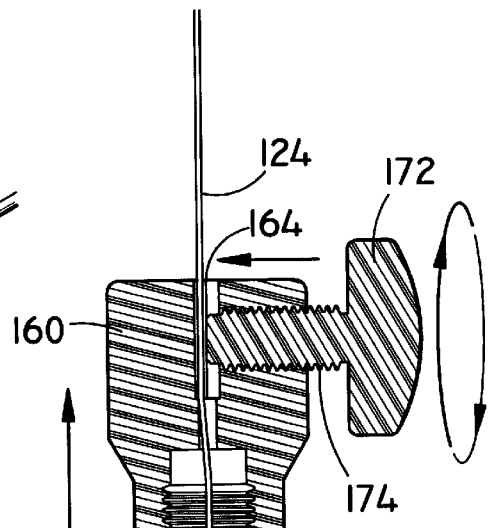
FIG. 15
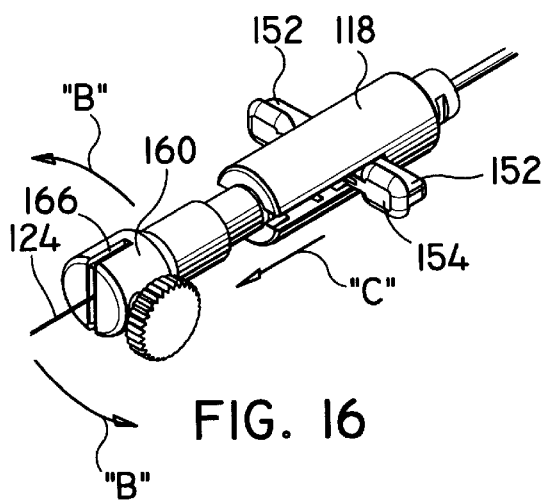
FIG. 16
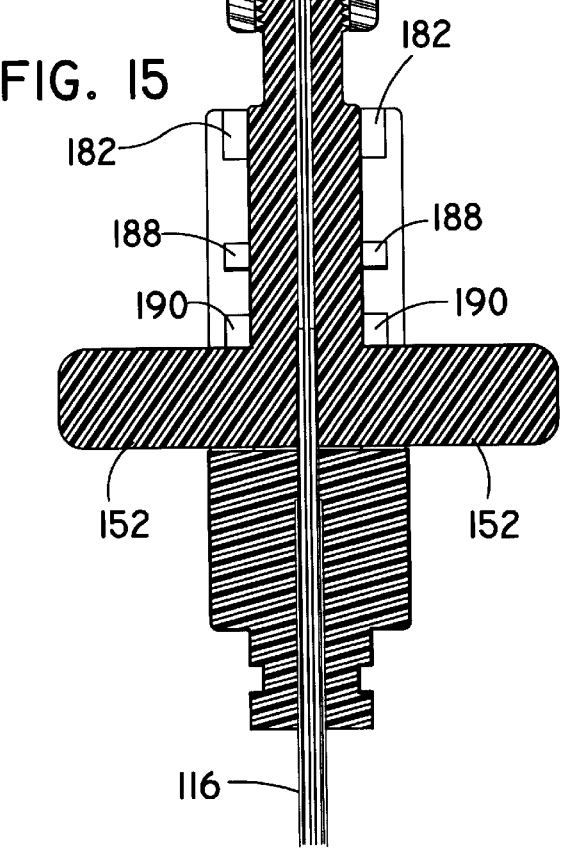

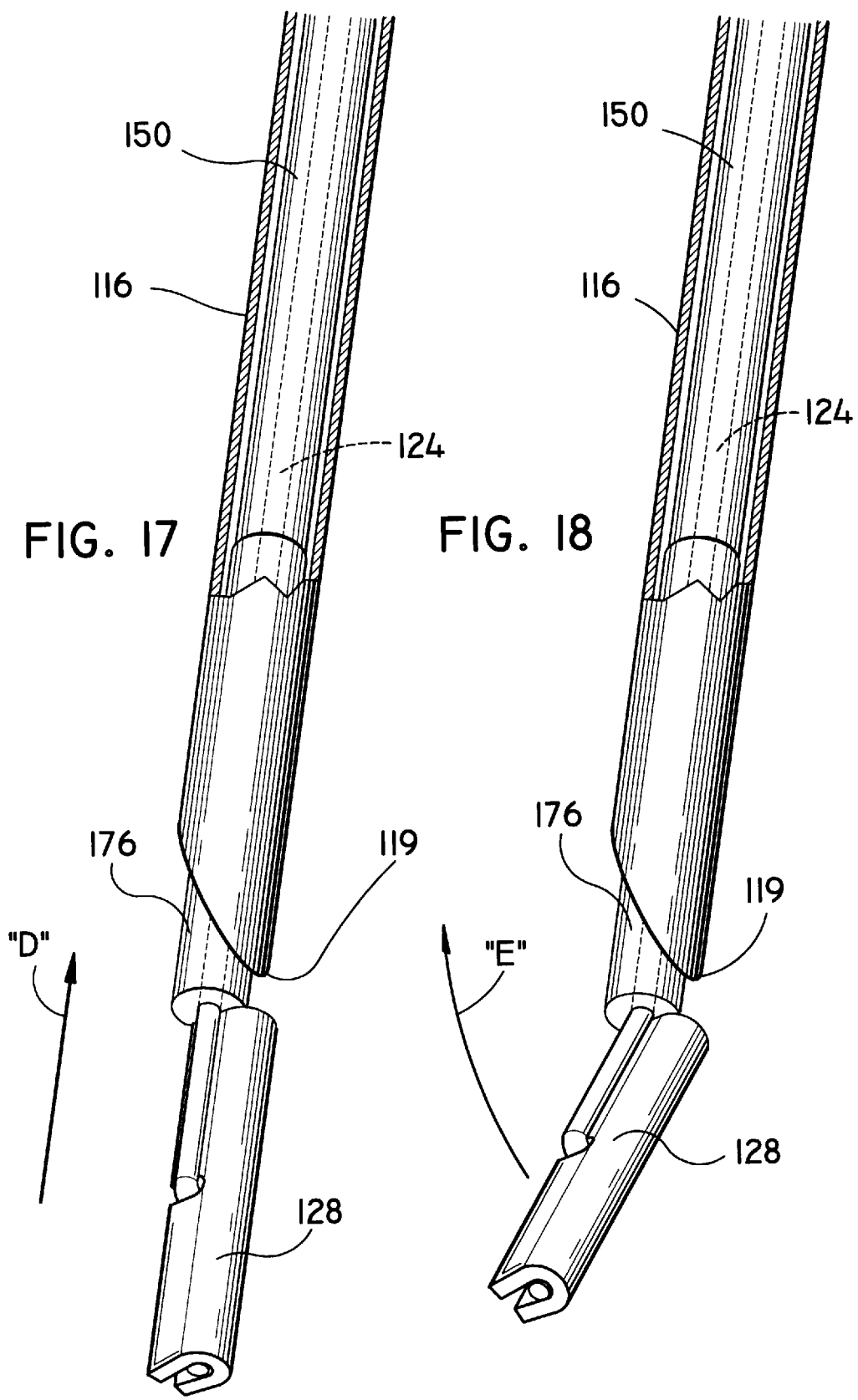

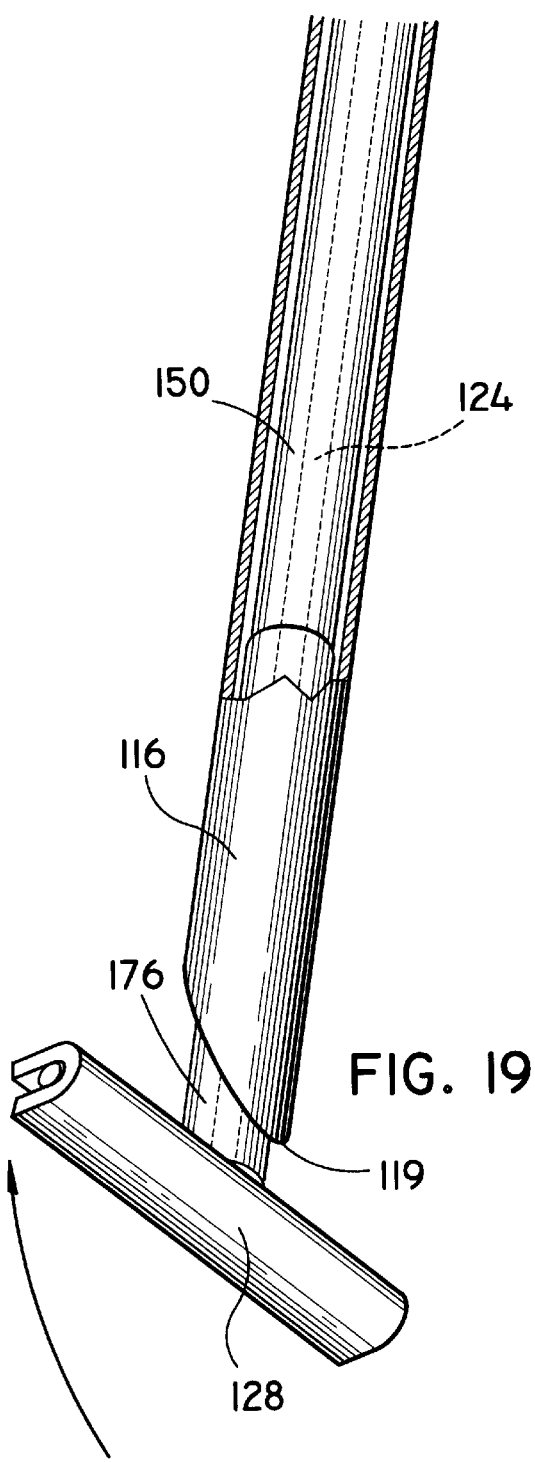
FIG. 19
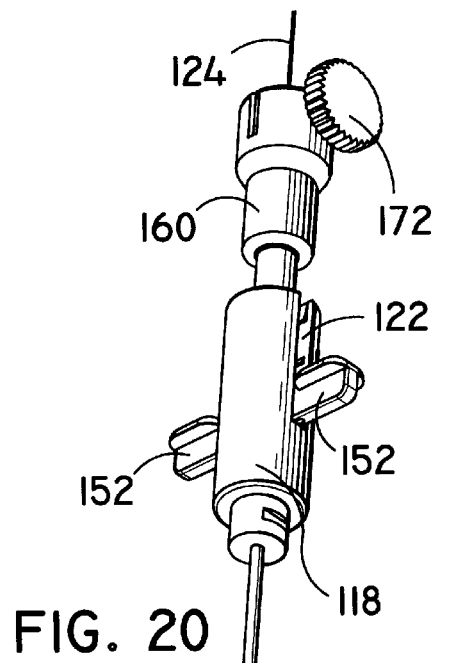
FIG. 20
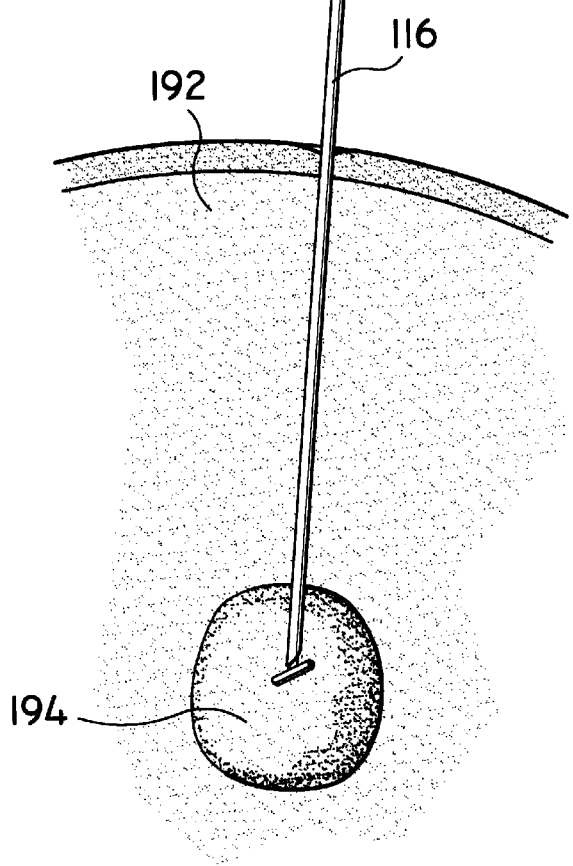

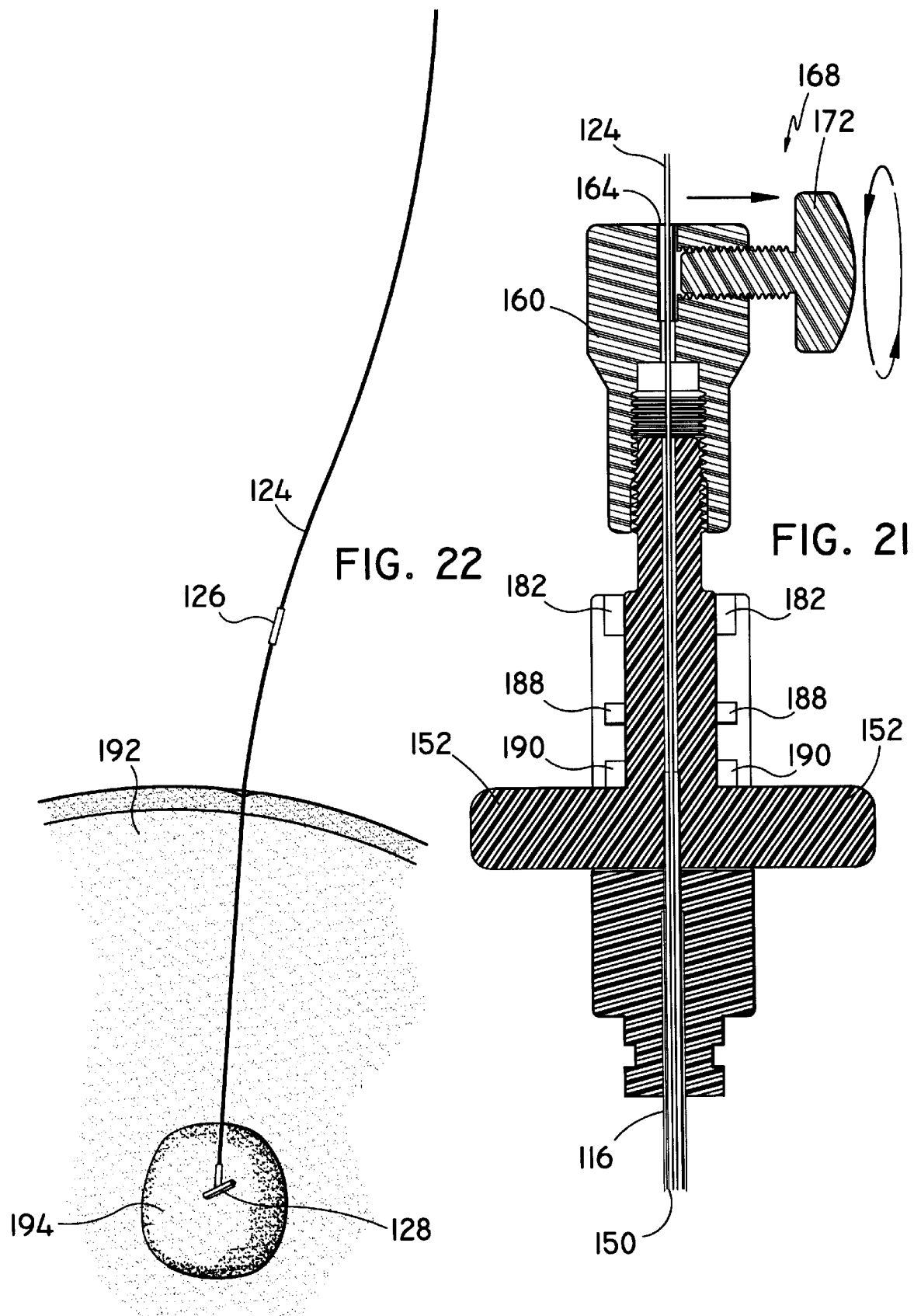

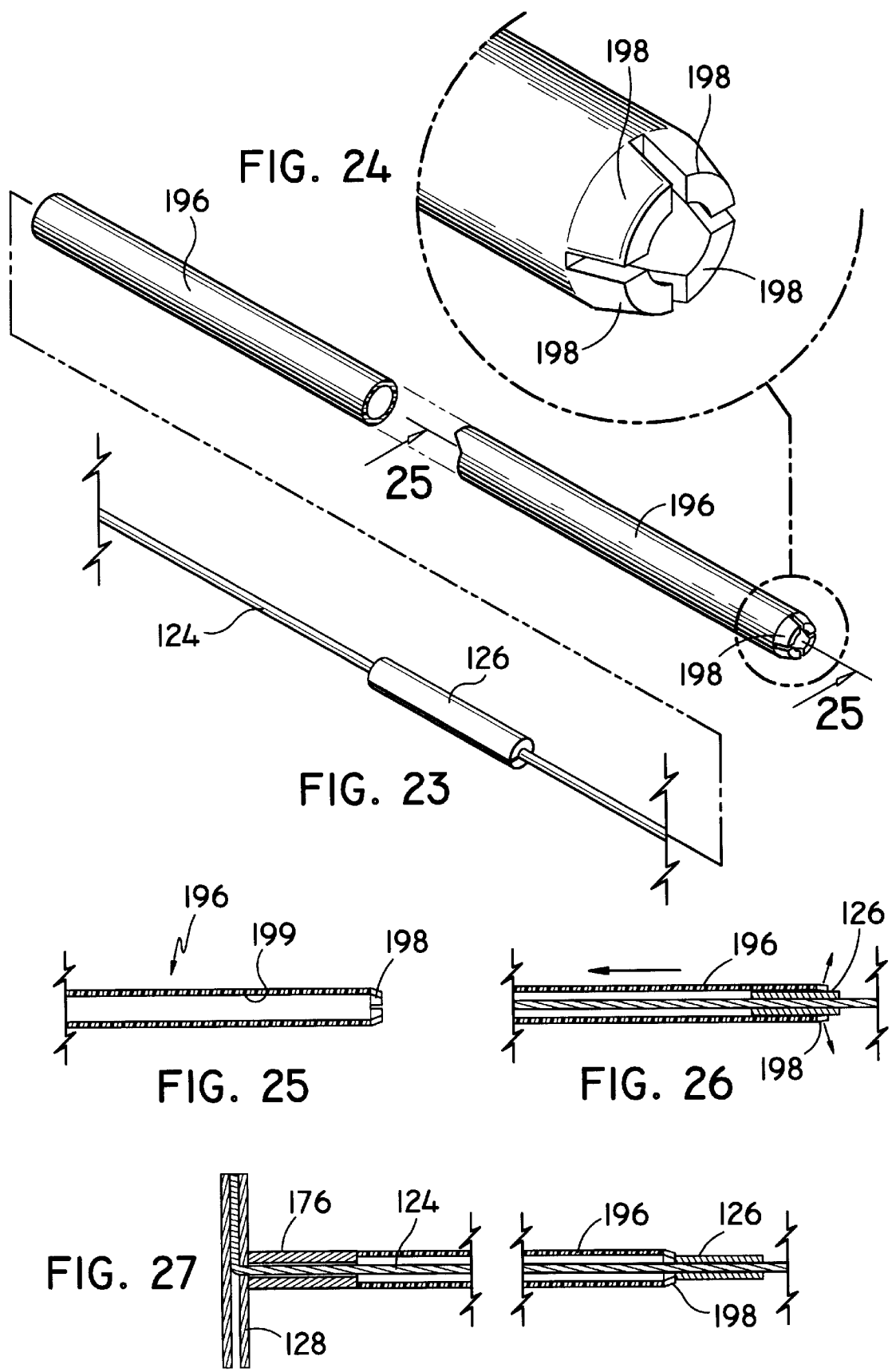

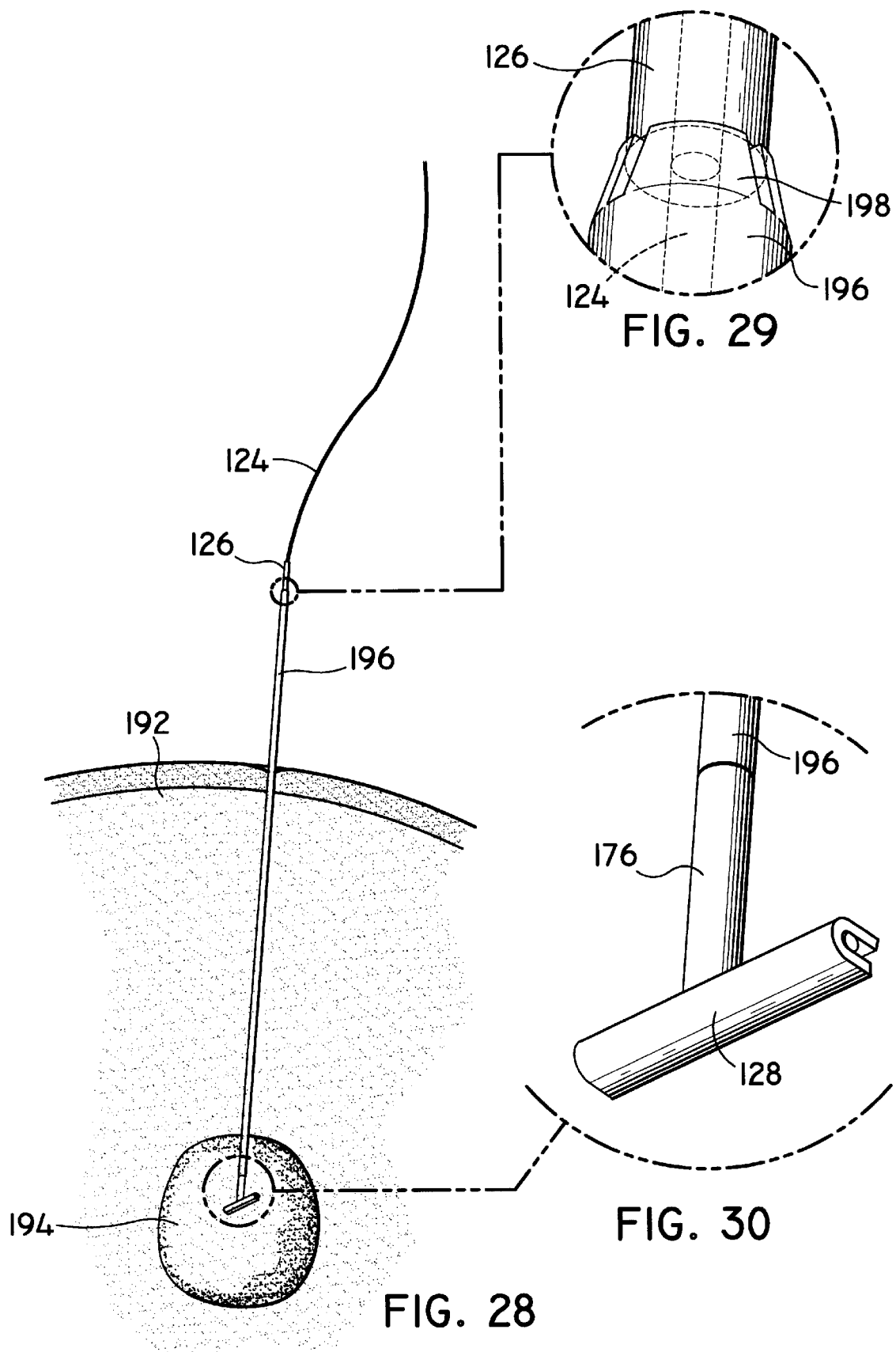

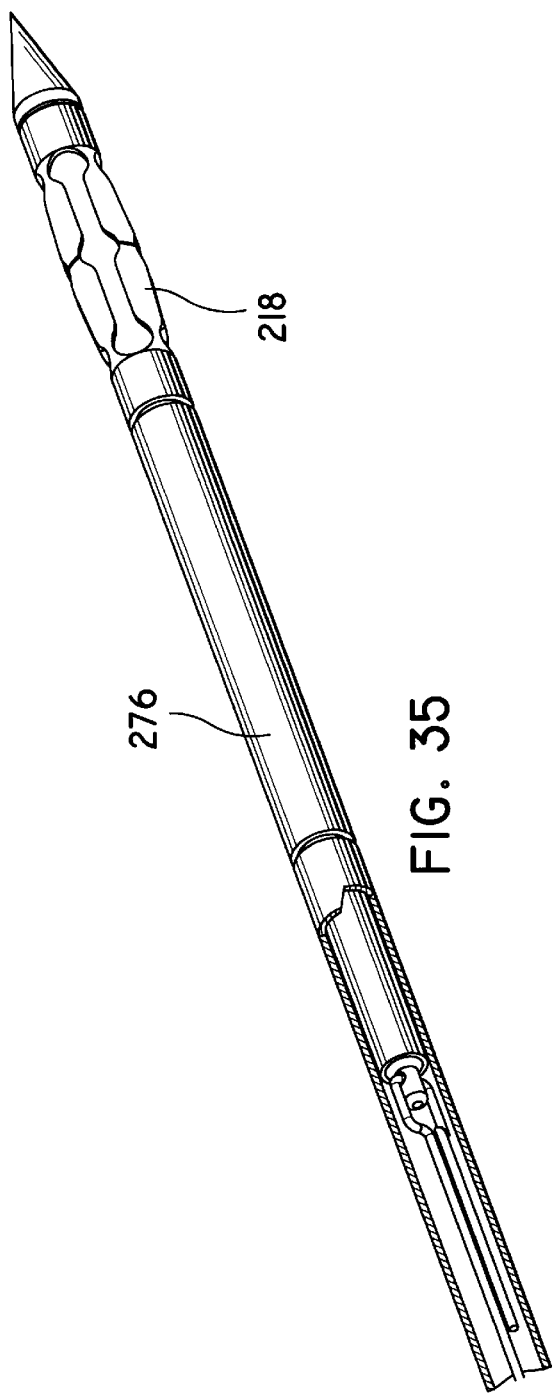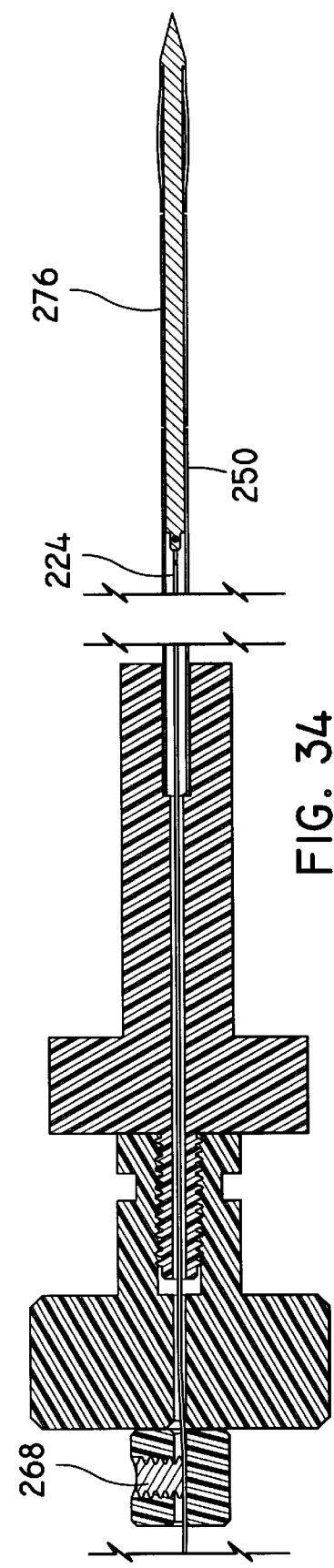

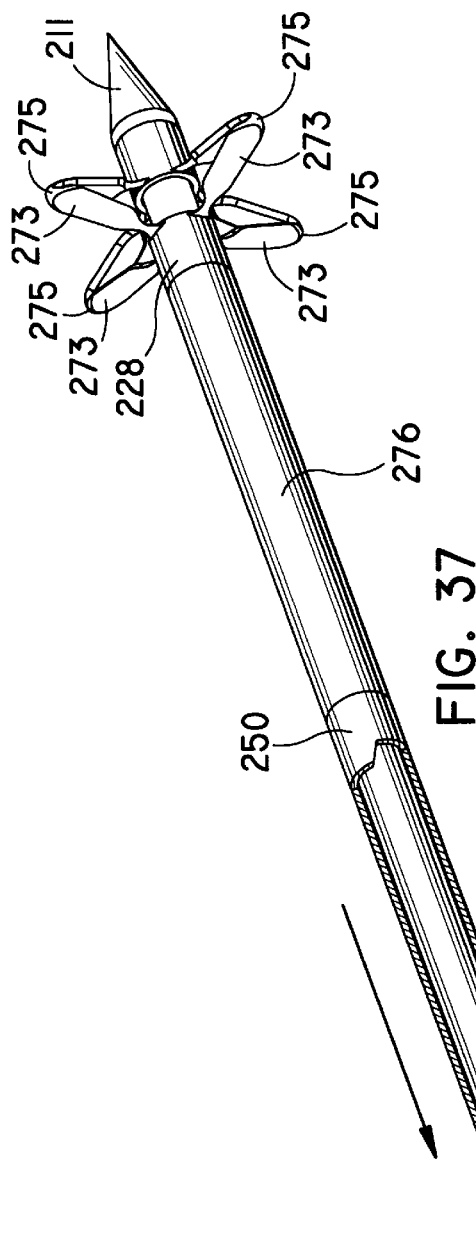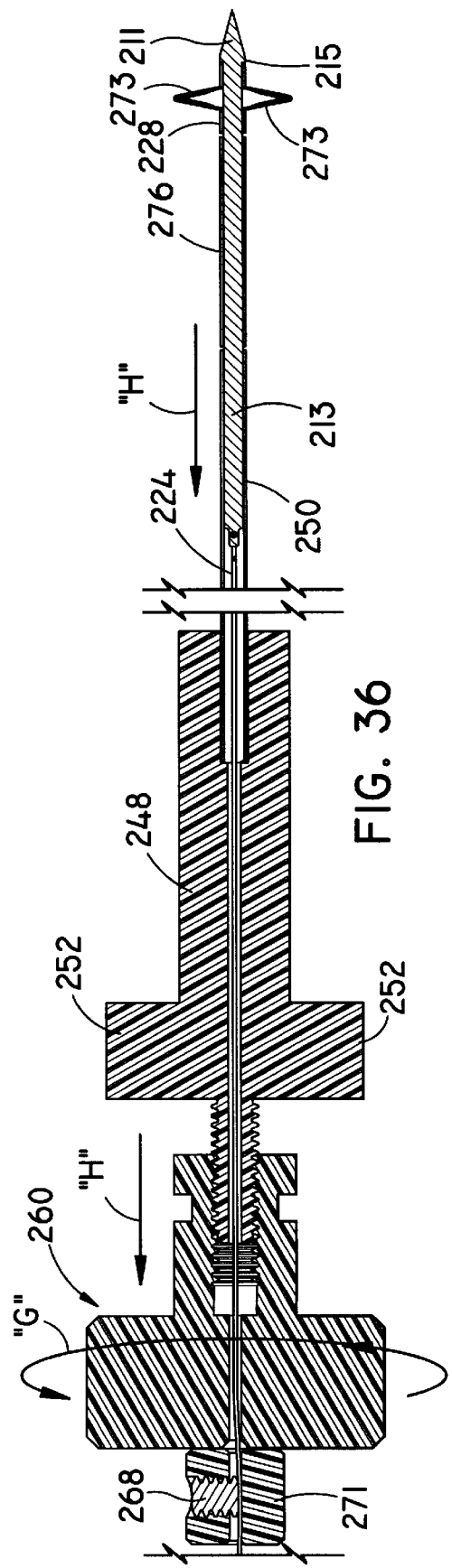

APPARATUS FOR MARKING TISSUE LOCATION

This is a continuation of application Ser. No. 08/823,889, filed Mar. 17, 1997, now abandoned, which is a continuation of copending application Ser. No. 08/546,483 filed on Oct. 20, 1995, now abandoned.

BACKGROUND

1. Technical Field

The present disclosure relates generally to tissue marking apparatus and method for identifying a particular location within a mass of body tissue.

2. Background of Related Art

Marking specific locations within body tissue, such as non-palpable lesions discovered within the body, and devices such as needles and wires for marking these lesions, are well known in the art. Such devices generally comprise a hypodermic needle or cannula which is inserted into the body and positioned adjacent to or in contact with the lesion. A wire marker is then passed through the needle or cannula and is anchored to the lesion marking it for subsequent surgical procedure, for example, excision or biopsy. Once the lesion is marked, the cannula is usually removed from the body, leaving the wire in place protruding from the body.

One of the most common procedures in which suspect tissue is marked is to locate potentially cancerous lesions found within a female patient's breast tissue. In such procedures, the subject breast is typically compressed during a mammographic tagging procedure. With some of the known devices, after the tissue marker is in place and compression discontinued, it is possible that the marker may dislodge or migrate from the position set during the tagging procedure.

Various tissue marking systems have been proposed to aid in locating non-palpable lesions within the breast and to prevent inadvertent dislodgment and/or migration of the needle. One such system includes a cannula needle and a wire guide made of a shape memory characteristic material which assumes a J-hook configuration. Such a device may be found, for example, in U.S. Pat. No. 5,011,473 to Gatturna which discloses a needle inserted into the breast and advanced to identify the location of a lesion. Gatturna discloses a wire which is advanced inwardly allowing a J-hooked end to engage body tissue and immobilize the needle.

Devices utilizing such J-hook systems, however, have been unable to solve the problem of preventing migration of the tissue marker. For example, in such devices, the tissue marker can be displaced if pressure is applied to the breast during transportation of the patient to the surgical suite or during preparation of the patient for surgery. Also, if the strength or resiliency of the wire is less than that required to penetrate the lesion, the hook may not reform, allowing the marker to migrate.

Another example of existing tissue marking devices, referred to as a needle and hook-wire system, may be found in U.S. Pat. No. 5,158,084 to Ghiatas. Ghiatas discloses a tissue-marking needle system which includes a stainless steel wire having a hairpin hooked-end. Similar to the J-hook system, the needle is inserted into the breast tissue to locate the lesion and the wire is slid through the needle thereby engaging the body tissue and anchoring the wire at lesion's location.

In such devices, however, compression of the breast, e.g., as routinely done during mammographic filming of the breast, may result in migration or displacement of the needle. Although the hook will tend to prevent outward movement of the wire, it is not designed to prevent advancement of the wire further into the patient's breast tissue.

Accordingly, a need exists for an improved tissue marking apparatus which overcomes the above-noted limitations of existing tissue marking devices, is easy to use and provides more reliability when marking suspect tissue.

SUMMARY

The present disclosure provides a surgical apparatus and a method for marking a particular location in body tissue, which addresses the limitations associated with conventional tissue marking devices. Additionally, the present disclosure provides a surgical apparatus for marking a location within tissue which may be used in both minimally invasive as well as open surgical procedures.

One embodiment of the present disclosure provides a surgical apparatus for marking a location within tissue, such apparatus including (i) a needle including a housing and an elongated tube having a sharp distal end, (ii) an elongated cable configured and dimensioned to pass through a longitudinal passageway formed through the needle, (iii) an elongated tissue marker attached adjacent a distal end of the elongated cable such that the elongated marker is movable between a retracted orientation and a deployed orientation, and (iv) an actuator assembly operatively associated with the elongated marker, wherein movement of the actuator assembly from a first position to a second position moves the elongated marker from the retracted position to the deployed position.

In a preferred embodiment, when the elongated marker is in the retracted position, a longitudinal axis of the elongated marker is substantially parallel to a longitudinal axis of the elongated cable. Additionally, when the elongated marker is in the deployed position, the longitudinal axis of the elongated marker is substantially perpendicular or transverse to the longitudinal axis of the elongated cable.

In an alternative embodiment, the elongated marker is movable between (i) a retracted position, wherein the elongated marker forms a substantially uniform transverse dimension, and (ii) a deployed position, wherein the elongated marker has a transverse dimension which is substantially greater than that of the outer surface of the elongated needle tube. Preferably, in the retracted position, the elongated marker includes an outer surface which is in substantial alignment with the outer dimension of the elongated needle tube which is used to introduce the elongated marker to the target tissue.

Preferably, the actuator assembly includes a first deployment actuator operatively connected to the housing and a second deployment actuator operatively associated with the first deployment actuator. The actuator assembly also preferably includes an advancing tube disposed between the first deployment actuator and the elongated marker.

The present disclosure also provides a surgical apparatus for marking a particular location in body tissue, which includes (i) a needle defining a longitudinal passageway therethrough, (ii) an elongated cable configured and dimensioned to pass through the longitudinal passageway, (iii) an elongated marker attached adjacent a distal end of the elongated cable such that the elongated marker is movable between a retracted orientation and a deployed orientation, and (iv) a stabilizer member which is moved from a first position relative to the elongated cable and the elongated marker, to a second position in operative association with the elongated cable and the elongated marker to maintain the elongated marker in the deployed orientation. The apparatus preferably also includes a stop member disposed on the elongated cable at a point proximal of the elongated marker, wherein the stabilizer member is disposed between the elongated marker and the stop member, such that the elongated cable is held in tension between the stop member and the elongated marker. Preferably, the stop member is a ferrule which is attached to the elongated cable member.

A clamp is also disclosed herein which is operatively associated with the elongated cable to selectively prevent longitudinal movement of the elongated cable relative to the needle. The clamp preferably includes a screw movable from a first position, which permits longitudinal movement of the elongated cable relative to the apparatus housing, to a second position, which prevents longitudinal movement of the elongated cable relative to the apparatus housing.

The present disclosure also provides an apparatus for marking a particular location in body tissue, which includes (i) a housing, (ii) an elongated cable configured and dimensioned to pass through a longitudinal passageway defined by the housing, (iii) a tissue marker operatively connected to a distal end of the elongated cable, such that movement of the elongated cable from a first position to a second position moves the marker from a retracted orientation to a deployed orientation, and (iv) a clamp operatively associated with the elongated cable to selectively prevent longitudinal movement of the elongated cable relative to the apparatus housing.

The clamp preferably includes a body portion defining a passageway therethrough to receive the elongated cable and a bias member movable from a released position, wherein the elongated cable is permitted to move longitudinally relative to the body portion and a clamped position, wherein the elongated cable is prevented from moving longitudinally relative to the body portion.

The present disclosure also provides a surgical apparatus for marking a particular location in body tissue, which includes (i) a needle assembly including a housing and an elongated tube having a sharp distal end, (ii) a marker assembly including an elongated cable configured and dimensioned to pass through a longitudinal passageway defined by the needle assembly, and an elongated tissue marker attached adjacent a distal end of the elongated cable such that the elongated marker is movable between a retracted orientation and a deployed orientation, wherein the elongated cable is sufficiently rigid to maintain the elongated tissue marker in each of said retracted and deployed orientations, and (iii) an actuator assembly operatively associated with the elongated marker, wherein movement of the actuator assembly from a first position to a second position moves the elongated marker from the retracted position to the deployed position.

The present disclosure also provides a method of marking a particular location in body tissue which includes the steps of (i) inserting an apparatus into a section of body tissue, (ii) deploying an elongated marker having an elongated cable attached thereto from the apparatus into the tissue, (iii) retaining the elongated cable relative to the distal end of the apparatus, and (iv) moving the elongated marker into an orientation substantially perpendicular to the elongated cable.

The method may further include the step of fixing the orientation of the marker in the deployed orientation. Preferably the step of retaining the elongated cable includes clamping the elongated cable to a portion of the apparatus.

BRIEF DESCRIPTION OF THE DRAWINGS

Various embodiments are described herein with reference to the drawings, wherein:

FIG. 2 is a perspective view, with parts separated, which shows the individual structural components of the embodiment of FIG. 1;

FIG. 3 is a partial perspective view, with parts separated, which shows the distal end of the cable of the embodiment of FIG.1 and the positioning of the tissue marker thereon;

FIG. 4 is a perspective view similar to FIG. 3, which shows the tissue marker crimped in place on the distal end of the cable;

FIG. 5 is a perspective view of the distal end of the apparatus embodiment of FIG. 1, which shows the relative positioning of the cable and tissue marker within the needle of the embodiment of FIG. 1;

FIG. 6 is a partial perspective view showing the proximal end of the embodiment of FIG. 1;

FIG. 7 is an enlarged view of the indicated area of detail of FIG. 6;

FIG. 8 is a partially cut-away perspective view which shows the internal working surfaces of the actuator housing;

FIG. 9 is an enlarged partially cut-away view of the indicated area of detail of FIG. 6;

FIG. 10 is a perspective view, which shows the insertion of the embodiment of FIG. 1 in the tissue of a patient to the location of the suspect tissue;

FIG. 11 is a partial cross-sectional view of the proximal end of the embodiment of FIG. 1;

FIG. 12 is a view similar to FIG. 11, showing actuator assembly deployment of the embodiment of FIG. 1;

FIG. 13 is a partially cut-away perspective view of the distal end of the embodiment of FIG. 1, which shows the corresponding movement of the tissue marker from a distal end of the apparatus as effected by the movement of the actuator assembly indicated in FIG. 12;

FIG. 14 is a perspective view of the proximal end of the apparatus which corresponds to the view of FIG. 12;

FIG. 15 is a longitudinal cross-section view of the proximal portion of the embodiment of FIG. 1, which shows the movement of the various operational components involved in deploying the tissue marker to its fully rotationally deployed position;

FIG. 16 is a perspective view of the proximal end of the embodiment of FIG. 1, which corresponds to the view shown in FIG. 15;

FIG. 17 is a perspective view of the distal end of the embodiment of FIG. 1, which shows the initial distally deployed position of the tissue marker immediately before rotational deployment thereof;

FIG. 18 is a view similar to FIG. 17, which shows the initial rotational deployment motion of the tissue marker;

FIG. 19 is a view similar to FIGS. 17 and 18, which shows the complete rotational deployment of the tissue marker;

FIG. 20 is a view similar to FIG. 10, which shows the tissue marker in its full rotationally deployed position within the suspect tissue lesion;

FIG. 21 is a longitudinal cross-sectional view of the proximal end of the embodiment of FIG. 1, which shows the release of the clamping mechanism on the cable;

FIG. 22 is a view showing the marker and cable in place in the suspect tissue lesion with the marking apparatus removed therefrom;

FIG. 23 is a perspective partially cut-away view, with parts separated, which shows the relationship of the crimped ferrule positioned on the cable and the stabilizing tube;

FIG. 24 is an enlarged view of the indicated area of detail of the distal of the stabilizing tube as indicated in FIG. 23;

FIG. 25 is a cross-section view taken along section line 25—25 of FIG. 23;

FIG. 26 is a cross-section view similar to FIG. 25, which shows the insertion of the stabilizing tube over the cable and crimped ferrule;

FIG. 27 is a broken longitudinal cross-sectional view, which shows the stabilizing tube in position between the ferrule member and the tissue marker;

FIG. 28 is a view similar to FIG. 22, which shows the stabilizing tube in place;

FIG. 29 is an enlarged view of the indicated area of detail shown in FIG. 28;

FIG. 30 is enlarged view of the fully deployed marker as shown in the indicated area of detail of FIG. 28;

FIG. 34 is a broken, longitudinal cross-sectional view of the embodiment of FIG. 31;

FIG. 35 is a perspective view, which shows the distal end of the embodiment of FIG. 31 with a portion of the advancing tube partially cut away;

FIG. 36 is a broken, longitudinal cross-sectional view showing the deployment of the tissue marker; and FIG. 37 is a perspective view similar to FIG. 35, which shows the deployment of the marker as corresponds to FIG. 36.

DETAILED DESCRIPTION OF PREFERRED EMBODIMENTS

Figure 1:
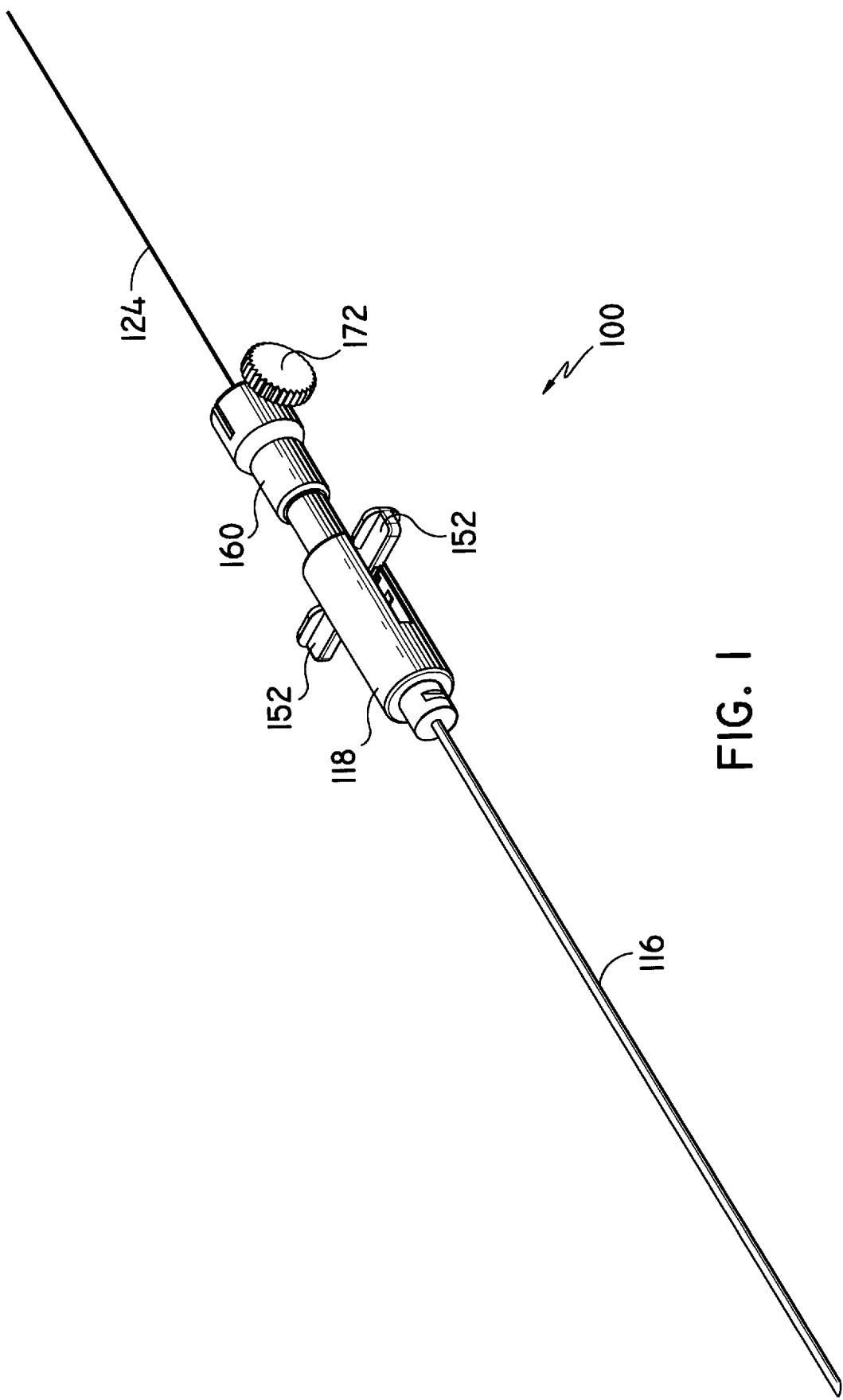
FIG. 1 is a perspective view of one embodiment of the apparatus for marking a particular location in body tissue constructed in accordance with the present disclosure.

Preferred embodiments of the presently disclosed tissue marking apparatus will now be described in detail with reference to the drawings, in which like reference numerals designate identical or corresponding elements throughout each of the several views. Referring initially to FIGS. 1 and 2, one embodiment of an apparatus for marking a particular location in body tissue in accordance with the present disclosure is exemplified by tissue marker apparatus 100. Tissue marker apparatus 100 is particularly adapted for use in minimally invasive surgical procedures to mark the location of targeted or suspect tissue.

The presently disclosed tissue marker apparatus embodiments are illustrated as utilized to locate lesions formed within the tissue of a female breast as identified by known imaging processes, e.g., stereotactic imaging. However, it will be understood by those skilled in the art that the presently disclosed tissue marker apparatus embodiments may also be utilized to locate targeted or suspect tissue in other areas of the body as well.

Except where noted otherwise, the materials utilized in the components of the presently disclosed embodiments of apparatus for marking particular locations in body tissue generally include materials such as polycarbonate for housing sections and related components and stainless steel for components that are required to cut tissue. A preferred polycarbonate material is available from General Electric under the trademark LEXAN.

Generally, tissue marker apparatus 100, when assembled into its three principle subassemblies, includes a needle assembly 110, a marker assembly 112, and an actuator assembly 114, as described in detail further herein.

As shown in FIG. 2, needle assembly 110 includes a hollow, preferably stainless steel, shaft 116 having a barrel-shaped body portion 118 mounted at a proximal end and a sharpened hollow tip 119 formed at a distal end. Body portion 118 preferably has a stepped throughbore 120 (FIG. 8) to securely receive shaft portion 116, e.g., by friction fit, which may be supplemented by bonding, adhesives or the like. Body portion 118 is further provided with a transverse slot 122 which is open at the proximal end surface of body portion 118. The significance of transverse slot 122 and the various control surfaces formed thereon are described in detail further herein.

Referring now to FIG. 2A through FIG. 5 in conjunction with FIG. 2, marker assembly 112 includes a cable 124, a stop member in the form of a ferrule 126 crimped around cable 124 at a predetermined distance from the distal end (as is explained further herein), and a tissue marker 128 crimped about the distal end portion 130.

As best illustrated in FIG. 3, tissue marker 128, in a preferred configuration, is formed to have an elongated longitudinal U-shaped channel 132 forming a pair of opposed flanges 134a and 134b. A notch 136 is formed at approximately the mid-point of flange 134a to facilitate the crimping of tissue marker 128 about the distal end portion 130 of cable 124. Tissue marker 128 could also have alternative configurations which would also facilitate its attachment to cable 124. For example, the distal end portion of tissue marker 128 could be pre-formed to have a hollow cylindrical configuration. The tissue marker could then be attached to cable 124 by, for example, swaging or welding.

Distal end portion 130 of cable 124 is provided with a series of bends to form elbows 138a, 138b, 140a, and 140b to accommodate marker assembly 112 within needle shaft 116, as shown in FIG. 5, and to facilitate deployment of tissue marker 128. Elbows 138a and 138b offset cable segment 142 a predetermined distance "X", as indicated in FIG. 3, from a proximal segment 144 of cable 124.

Thus, when tissue marker 128 is fitted over distal end portion 130 of cable 124, the portion of tissue marker 128 proximal of notch 136 is disposed entirely on one side of cable segment 142, as shown in FIG. 4. Elbows 140a and 140b offset cable segment 146 a predetermined distance "Y" from proximal cable segment 144. Distance "Y" is preferably less than distance "X", such that cable segment portion 146 fits within elongated U-shaped channel 132 and flange portions 134a and 134b are crimped about segment 146 as shown in FIG. 4. Distances "X" and "Y" are predetermined such that upon assembly with cable 124 tissue marker 128 is substantially parallel to proximal cable segment 144 the assembled cable 124 and tissue marker 128 fit within the internal diameter of needle shaft 116, as shown in FIG. 5.

Actuator assembly 114 will now be described with reference to FIG. 2 in conjunction with FIGS. 6–8. A plunger 148 is provided which includes a longitudinal throughbore formed therein. An elongated advancing tube 150 is preferably friction fitted in the distal end of the throughbore of plunger 148. Alternatively, advancing tube 150 may be secured in the throughbore of plunger 148, for example, by bonding, adhesives, sonic welding or the like.

Plunger 148 is preferably provided with transversely extending deployment arms 152. A pair of bearing surfaces 154 are formed on the proximal surface of deployment arms 152 and are preferably configured and dimensioned to facilitate ergonomic distal movement of plunger 148. For example, bearing surfaces are preferably formed to be comfortably engaged by a finger of the user. Thus deployment arms may be moved distally by the user applying pressure on bearing surfaces 154 with a finger or fingers. Plunger 148 is further provided with a reduced diameter portion 156 extending from a proximal end and having threads 158 formed at the proximal end thereof. Threads 158 engage internal threads 162 formed along the distal end inner surface of a stepped throughbore formed in marker deployment actuator 160.

A cable clamp mechanism is also provided on marker deployment actuator 160 and includes a U-shaped stainless steel clip 164 which is fitted in a transversely extending slot 166 which is open at the proximal end surface of marker deployment actuator 160. A clamp set-screw 168 also forming part of the clamp mechanism is provided to be threadably received in a threaded bore 170 formed through marker deployment actuator 160. Threaded bore 170 is formed transverse to slot 166 and extends from an inner wall of slot 166 to the outer longitudinal surface of marker deployment actuator 160. The significance of the clamp mechanism will be described in further detail herein. Preferably, clamp set screw 168 is provided with a knurled dial 172 attached to threaded portion 174 to facilitate actuation of the clamping mechanism upon rotation of knurled dial 172 by the user.

Referring temporarily back to FIG. 5, an abutment member 176, which also forms part of the actuator assembly 114, is slidably positioned on cable 124 between distal end portion 130 and crimped ferrule 126. Abutment member 176 is preferably formed as an elongated cylindrically shaped element having a longitudinal throughbore formed therein. The wall thickness of abutment member 176 is preferably greater than the wall thickness of advancing tube 150. Additionally, the throughbore of abutment member 176 is dimensioned to be only slightly greater than the outer diameter of proximal cable segment 144. For example, a suitable tolerance between the throughbore of abutment member 176 and the outer diameter of proximal cable segment 144 is approximately 0.01–0.05 mm. This dimensional relationship between the throughbore of abutment member 176 and proximal cable segment 144 facilitates the rotational deployment of tissue marker 128 while providing additional stability, as will be described further herein.

Actuator assembly 114 is advantageously designed to provide a two-stage actuation to place tissue marker 128 at the desired location. In the first stage, plunger 148 is moved distally to longitudinally deploy tissue marker 128 and cable 124 from the distal end of needle shaft 116. In the second stage, proximal cable segment 144 is clamped to marker deployment actuator 160 by clamp set-screw 168 and marker deployment actuator 160 is moved proximally, for example, by rotating marker deployment actuator 160 relative to plunger 148 so as to separate the two components. This motion pulls cable 124 and tissue marker 128 proximally with respect to abutment member 176. Alternatively, marker deployment actuator 160 may be slidably disposed relative to plunger 148 to effectuate the desired proximal movement.

During the second stage of actuation, it is necessary to maintain plunger 148 in a fixed relationship relative to needle assembly 110. Accordingly, body portion 118 of needle assembly 110 is provided with several control surfaces to facilitate deployment of marker assembly 112 from the distal end of needle assembly 110 and to maintain the relative positioning of plunger 148 with respect to needle assembly 110.

Referring to FIGS. 6–8, body portion 118 is provided with a series of wedge-shaped stops formed along the inner surfaces 178 and 180 of transverse slot 122. A first group of stops 182 formed in opposing relationship at the same axial disposition along inner surfaces 178 and 180 establish the initial pre-deployed position of plunger 148 which corresponds to the fully retracted position of marker assembly 112 as shown in FIG. 5. Stops 182 additionally facilitate assembly of actuator assembly 114 into body portion 118. Camming action caused by arms 152 as plunger 148 is inserted in the open end of slot 122 until the proximal surface of arms 152 pass beyond the distal face of stops 182. Once arms 152 are inserted past stops 182, opposed barrel portions 184 and 186 snap back into place, thereby preventing proximal movement of plunger 148.

A second or intermediate group of stops 188 which are somewhat smaller than stops 182 are formed along inner surfaces 178 and 180 at the same axial disposition relative to each other. Stops 188 are spaced a distance distally from stops 182 such that arms 152 are disposed between the distal face of stops 182 and the proximal-most portion of stops 188. Plunger 148 is thereby maintained at the initial pre-deployment position of marker assembly 112, as shown in FIG. 5.

A third group of stops 190 are provided along the inner walls 178 and 180 at the same axial disposition relative to each other to define a second position for plunger 148 corresponding to a distally deployed orientation of marker assembly 112 (as shown in FIG. 13). Similar to stops 182 and 188, stops 190 are formed in the shape of a wedge to facilitate distal movement of plunger 148 by camming barrel portions 184 and 186 outwardly as arms 152 pass over stops 190. Once arms 152 pass beyond the distal faces of stops 190, barrel portions 184 and 186 return to their at rest configurations thereby preventing proximal movement of plunger 148 relative to barrel portion 118.

In use, as shown in FIGS. 10–22, tissue marker apparatus 100, is inserted through the breast tissue 192 of a patient with its control surfaces initially configured as shown in FIGS. 10 and 11. Tissue marker apparatus 100 is inserted such that the distal end is positioned adjacent a suspect lesion 194. The exact location of lesion 194 may be identified by any suitable known imaging apparatus or process, such as by stereotactic mammographic imaging, as is known in the art.

As shown in FIGS. 12–14, marker assembly 112 is deployed from its initial position, through the first stage of deployment, i.e., distal movement to completely expose tissue marker 128 relative to the sharpened tip 119 of needle shaft 116. The exposure of tissue marker 128 is facilitated by applying a distally directed force to arms 152, as indicated by arrows "A" in FIG. 12. Marker assembly 112 is configured and dimensioned to reach its distal-most longitudinally deployed position when arms 152 abut against the bottom of slot 122. Stops 190 prevent plunger 148 and, therefore, advancing tube 150, abutment member 176 and finally tissue marker 128 from movement in a proximal direction once distally deployed.

Cable 124 and, therefore, marker assembly 112 are fixed with respect to marker deployment actuator 160 by applying the clamp mechanism provided on marker deployment actuator 160. Specifically dial 172 is rotated, as shown in FIG. 15, to advance set-screw 168 and clamp cable 124 between the sides of U-shaped clip 164.

The rotational deployment of tissue marker 128 is initiated by rotation of marker deployment actuator 160 relative to body portion 118, as indicated by arrows "B", FIG. 16, in a counterclockwise fashion to unthread deployment actuator 160 from body portion 118. This rotational movement imparts proximal movement, as indicated by arrow "C" in FIG. 16, of marker deployment actuator 160 and the clamped elongated cable 124 held therein. Marker assembly 112 is thereby pulled proximally with respect to the relatively fixed abutment member 176 as indicated by arrow "D" as shown in FIG. 17. Rotation of marker deployment actuator 160 will twist cable 124 which is preferably selected to have material characteristics which permit such twisting while maintaining the necessary tensile strength to hold tissue marker 128 in the fully deployed perpendicular position, as described below.

Upon continued rotation of marker deployment actuator 160 and proximal movement of marker assembly 112, cable 124 moves toward abutment member 176 so that elbows 138*a* and 138*b* (FIG. 5) are straightened due to the inner walls of the throughbore in abutment member 176 acting on the malleable cable 124. As shown in FIG. 18, once tissue marker 128 comes into abutment with the distal face of abutment member 176, continued rotation of marker deployment actuator 160, as shown in FIG. 16, causes tissue marker 128 to begin rotating in the direction indicated by arrow "E" shown in FIG. 18. This rotation is due to the offset parallel axial alignment of tissue marker 128 with respect to proximal segment 144 of cable 124 and abutment member 176.

Upon still further rotation of marker deployment actuator 160, tissue marker 128 becomes disposed perpendicular to abutment member 176, as shown in FIGS. 19 and 20, thereby preventing further rotation of actuator 160. The resistance to further rotation will provide indication to the user of the full deployment of tissue marker 128.

Once the marker assembly 112 is fully deployed as shown in FIGS. 19 and 20, the clamp mechanism may be released by unscrewing set screw 168 as shown in FIG. 21. With cable 124 released, apparatus 100 can be removed from cable 124 and the marker assembly 112 left in place as shown in FIG. 22.

The presently disclosed tissue marker apparatus 100 utilized in either a minimally invasive or an open biopsy procedure. In a minimally invasive procedure, the suspect tissue or lesion is preferably located by a stereotactic imaging apparatus and removed with a minimally invasive instrument used in conjunction with the stereotactic apparatus.

For example, the presently disclosed tissue marking apparatus 100 is designed to be used in conjunction with a minimally invasive breast biopsy device, such as is disclosed in currently pending, commonly assigned U.S. patent application Ser. No. 08/525,450, filed on Sep. 8, 1995 by Milliman et al., and commonly assigned, co-pending, U.S. patent application Ser. No. 08/546,482, concurrently filed herewith by Milliman et al., which is a continuation-in-part application of the former cited Milliman et al. application. The entire contents of each of these applications are hereby incorporated by reference. In such a minimally invasive biopsy procedure, the presently disclosed tissue marker apparatus 100 is deployed as set forth herein, the needle assembly 110 and actuator assembly 114 (except for the abutment member 176) are removed from the patient leaving the abutment member 176 and marker assembly 112 to mark the lesion location. Then the minimally invasive biopsy instrument embodiment adapted for use on a stereotactic imaging apparatus, as disclosed in the above-mentioned Milliman et al. applications, may be advanced into the breast using the cable 124 as a guide. The precision locating capabilities of the stereotactic imaging machine can then be used to insert the biopsy instrument to the appropriate depth prior to actuation of the tissue removal structure.

Alternatively, the presently disclosed tissue marker apparatus 100 may be utilized in an open breast biopsy procedure, i.e., a procedure wherein the patient will likely be taken into a surgical suite after the marker is deployed. In such a procedure the lesion may be located by any suitable imaging apparatus or process, for example stereotactic imaging or ultrasound. The tissue marker 128 is then deployed as set forth above, the needle assembly 110 and the actuation assembly 114 (except for abutment member 176) are removed from the patient, preferably before transporting the patient to the operative suite, if such transportation is necessary. Marker assembly 112 is thereby left in place with the abutment member 176 disposed around cable 124 adjacent the perpendicularly disposed marker 128. When the patient is located in the operating room, a stabilizing tube 196 is provided such as the one shown in FIGS. 23–30, which will now be described in detail. The lesion is then removed by cutting away the tissue leading to the lesion and then removing the lesion.

Referring initially to FIGS. 23–25, stabilizing tube 196 is formed as an elongated hollow tube having an open distal end and a substantially frustoconical open proximal end portion, preferably formed of a series of resilient tapered arcuate segments 198. Inner diameter 199 of stabilizing tube 196 is preferably slightly larger than the outer diameter of ferrule 126 to facilitate the insertion of stabilizing tube 196 over ferrule 126.

Specifically, once tissue marker 128 is properly positioned, the user can then stabilize the location of marker 128 by inserting the proximal segment 144 of cable 124 through the open distal end of stabilizing tube 196 and sliding stabilizing tube 196 over cable 124 such that the open end thereof passes completely past ferrule 126. This causes segments 198 to cam radially outwardly as shown in FIG. 26.

Figures 31, 32:
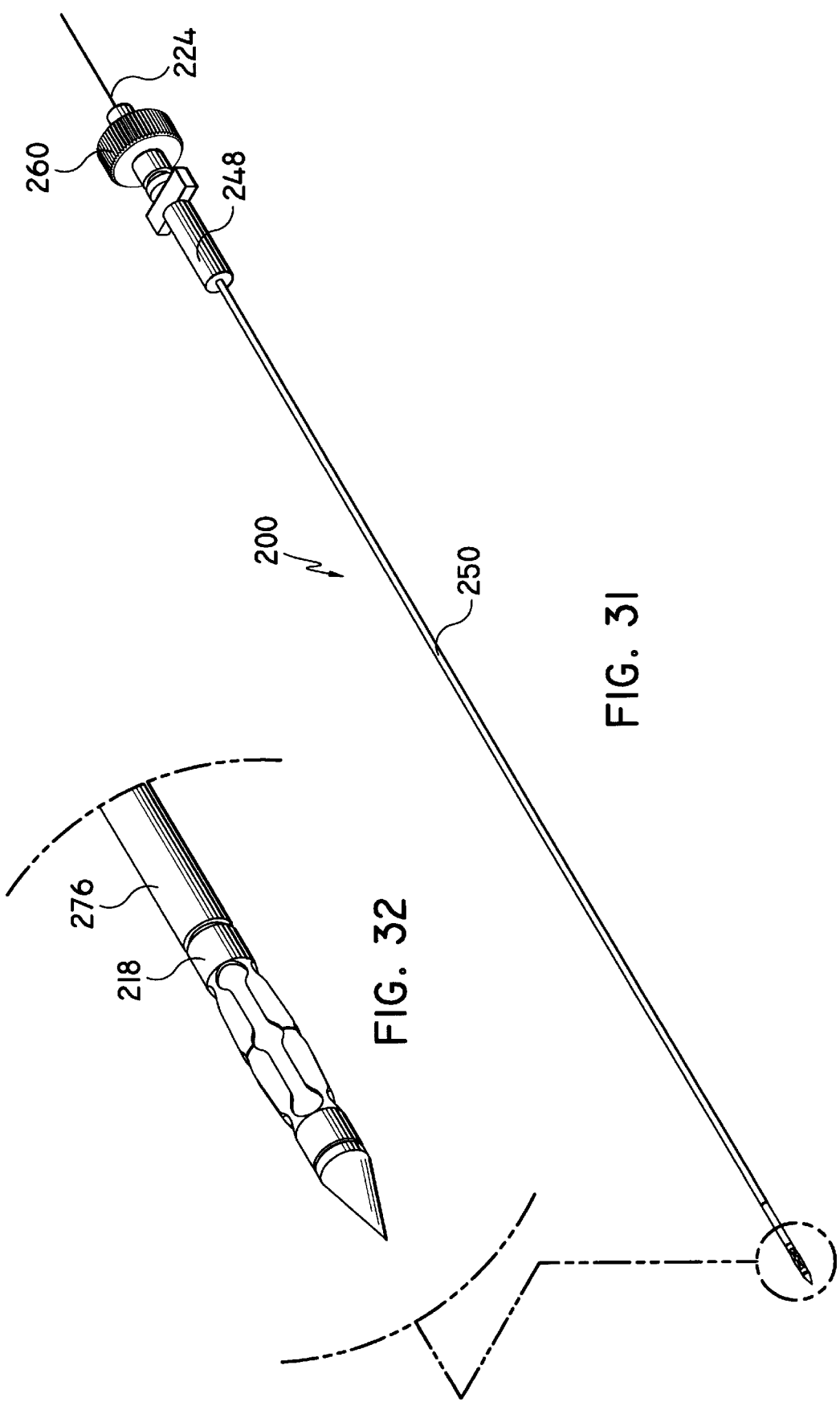
FIG. 31 is a perspective view of a further embodiment of an apparatus for marking a particular location in body tissue constructed in accordance with the present disclosure.
FIG. 32 is an enlarged view of the distal end of the embodiment of FIG. 31 as indicated by the area of detail in FIG. 31.
Figure 33:
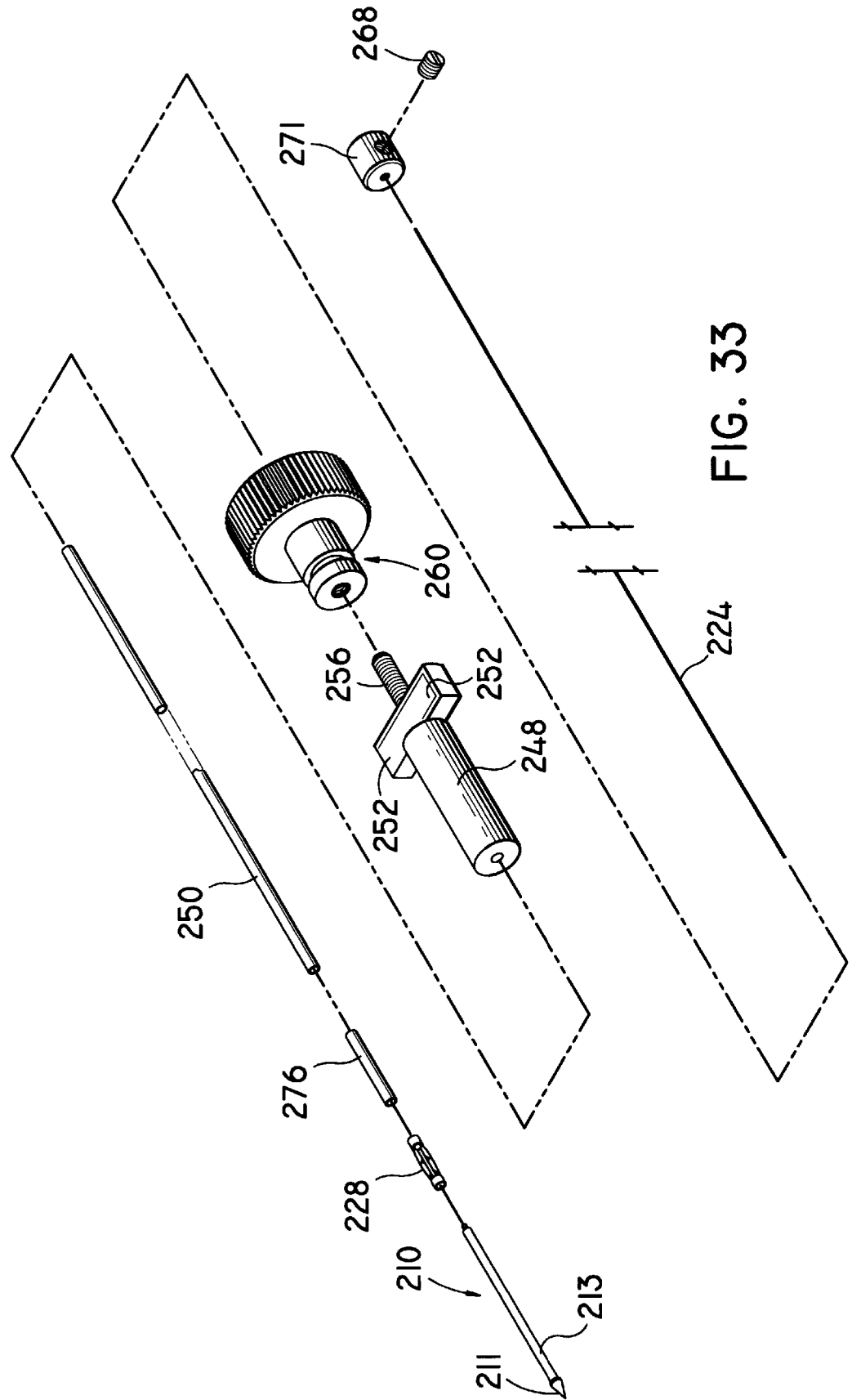
FIG. 33 is a perspective view with parts separated, which shows various components of the embodiment of FIG. 31.

Referring to FIG. 27, once the proximal end of stabilizing tube 196 passes distal of the distal end of ferrule 126, segments 198 are restored to their initial configuration thereby locking stabilizing tube 196 between ferrule 126 and abutment member 176. Tissue marker 128 is thus maintained perpendicular to abutment member 176 as shown in FIGS. 27–30 and cable 124 and is held in tension. Thereafter, A further embodiment of a surgical apparatus for marking a particular location in body tissue constructed in accordance with the present disclosure will now be described with reference to FIGS. 31–37. Referring to FIGS. 31–33, tissue marker apparatus 200 includes a needle 210 having a sharpened distal end point 211 and a cable 224 secured to a proximal end of needle 210. Tip 211 is preferably conically shaped and extends beyond the diameter of body portion 213 of needle 210 forming an annular shoulder 215 (FIG. 36). A tissue marker 228 is slidably disposed over body portion 213 of needle 210 and is positioned in abutment with annular shoulder 215. An abutment member 276 is having a longitudinal throughbore is slidably disposed over body portion 213 of needle 210, adjacent the proximal end of tissue marker 228. The aforementioned assembly of components is passed through an advancing tube 250 which is securely mounted, e.g., by friction fit in the distal portion of a stepped throughbore formed in a housing 248. Housing 248 is provided with transversely extending projections 252 at a proximal end thereof and proximally extending threaded portion 256. A marker deployment actuator 260 having a longitudinal throughbore formed therein with threads formed along the inner surface near the distal end of the longitudinal throughbore is threadably mounted on threaded portion 256 of body 248. End cap 271 is provided having a longitudinal throughbore formed therein to receive cable 224 therethrough. A set screw 268 is also provided and is threadably received in a transverse threaded bore formed through the sidewall of cap 271 to clamp cable 224 to cap 271 so as to maintain connection of needle 210 and tissue marker 228 to tissue marker apparatus 200.

Tissue marker 228 preferably has a series of longitudinal slats 273 which may be formed as bisected segments connected by a reduced cross-sectional dimension portion, commonly referred to as a "living hinge" 275, to facilitate expansion of slats 273 upon deployment of tissue marker 228.

In use, as shown in FIGS. 36 and 37, tissue marking apparatus 200 is inserted in the patient's breast in a manner similar to that for tissue marker apparatus 100 in the previously described embodiment. Once tissue marker 228 is positioned adjacent the suspect lesion, marker deployment actuator 260 is rotated, as indicated by arrow "G" in FIG. 36. This rotational motion causes marker deployment actuator 260 to move in a proximal direction, as indicated by arrow "H", due to the threading of marker deployment actuator 160 and body 248. With cable 224 held fixed relative to marker deployment actuator 260 by set screw 268, body portion 213 of needle 210 is also pulled proximally as indicated by arrow "H" shown in FIG. 36. Tissue marker 228 is thereby compressed causing slats 273 to expand radially outwardly thereby marking the suspect lesion location.

It will be understood that various modifications may be made to the embodiments disclosed herein. For example, the cable is preferably formed of an elongated wire segment, however numerous different types of cable may be utilized, such as multi-strand braided wire. Therefore, the above description should not be construed as limiting, but merely as exemplifications of preferred embodiments. Those skilled in the art will envision other modifications within the scope and spirit of the claims appended hereto.

What is claimed is:

1. A surgical apparatus for marking a particular location in body tissue, which comprises:
    a needle including a housing and an elongated tube having a sharp distal end, the housing and elongated tube forming a longitudinal passageway therethrough;
    an elongated cable configured and dimensioned to pass through the longitudinal passageway;
    an elongated tissue marker attached adjacent a distal end of the elongated cable such that the elongated marker is movable between a retracted orientation disposed within the elongated tube and substantially aligned with a longitudinal axis of the tube, an intermediate position disposed outside the elongated tube a distance away from the distal end of the elongated tube maintained in alignment with the longitudinal axis of the tube and a deployed orientation non-aligned with the tube longitudinal axis;
    wherein the elongated cable is sufficiently rigid to maintain the alignment of the marker with the longitudinal axis of the elongated tube, independently of the elongated tube, after the marker has been moved to the intermediate position disposed a distance away from the distal end of the elongated tube; and
    an actuator assembly operatively associated with the elongated marker and including first and second control portions, wherein relative movement of the first and second control portions from a first orientation to a second orientation moves the elongated marker from the retracted to the intermediate position and wherein further relative movement of the first and second control portions from the second orientation to a third orientation moves the elongated tissue marker to the deployed orientation.

2. A surgical apparatus for marking a particular location in body tissue according to claim 1, wherein when the elongated marker is in the retracted orientation a longitudinal axis of the elongated marker is substantially parallel to a longitudinal axis of the elongated cable.

3. A surgical apparatus for marking a particular location in body tissue according to claim 1, wherein when the elongated marker is in the deployed orientation a longitudinal axis of the elongated marker is substantially perpendicular to a longitudinal axis of the elongated cable.

4. A surgical apparatus for marking a particular location in body tissue according to claim 1, wherein the elongated marker is collapsible from the retracted orientation, wherein the elongated needle tube defines an outer surface and the elongated marker forms a substantially uniform transverse dimension with the outer surface of the elongated needle tube to the deployed orientation wherein the elongated marker has a transverse dimension which is substantially greater than that of the outer surface of the elongated needle tube.

5. A surgical apparatus for marking a particular location in body tissue according to claim 1, wherein the actuator assembly further includes an advancing tube disposed between the first control portion and the elongated marker.

6. A surgical apparatus for marking a particular location in body tissue according to claim 1, wherein the first deployment actuator is slidable with respect to the housing.

7. A surgical apparatus for marking a particular location in body tissue according to claim 1, wherein the first control portion is movable in either a proximal direction or a distal direction such that distal movement of the first control portion moves the elongated marker from the retracted orientation to the intermediate position a predetermined distance away from the sharp distal end of the elongated tube.

8. A surgical apparatus for marking a particular location in body tissue according to claim 1, wherein the second control portion is movable from a first position to a second position wherein such movement rotates the elongated marker from a first orientation to a second orientation.

9. A surgical apparatus according to claim 1, which further comprises a clamp operatively associated with the elongated cable to selectively prevent longitudinal movement of the elongated cable relative to the needle.

10. A surgical apparatus for marking a particular location in body tissue according to claim 9, wherein the clamp includes a screw movable from a first position which permits longitudinal movement of the elongated cable relative to the needle housing, to a second position which prevents longitudinal movement of the elongated cable relative to the needle housing.

11. A surgical apparatus according to claim 1, wherein movement of the tissue marker by the actuator assembly is effected by abutment of at least a portion of the actuator assembly with the tissue marker.

12. A surgical assembly for marking a particular location in body tissue, which comprises:

a needle defining a longitudinal passageway therethrough;

an elongated cable configured and dimensioned to pass through the longitudinal passageway;

an elongated marker attached adjacent a distal end of the elongated cable such that the elongated marker is movable between a retracted orientation and a deployed orientation;

wherein the elongated cable is sufficiently rigid to maintain the alignment of the marker with the longitudinal axis of the elongated tube, independently of the elongated the tube, after the marker has been moved to the intermediate position disposed a distance away from the distal end of the elongated tube; and a stabilizer member disposed in the longitudinal passageway and movable from a first position spaced away from the elongated marker, to a second position biased against the elongated marker to maintain the elongated marker in the deployed orientation such that body tissue disposed proximally of the elongated marker is not compressed by the stabilizer member.

13. A surgical apparatus for marking a particular location in body tissue according to claim 12, which further comprises a stop member disposed on the elongated cable at a point proximal of the elongated marker, wherein the stabilizer member is disposed between the elongated marker and the stop member such that the elongated cable is held in tension between the stop member and the elongated marker.

14. A surgical apparatus for marking a particular location in body tissue according to claim 13, wherein the stop member is a ferrule which is attached to the elongated cable.

15. A surgical apparatus for marking a particular location in body tissue according to claim 12, which further comprises a clamp operatively associated with the elongated cable to selectively prevent longitudinal movement of the elongated cable relative to the needle.

16. A surgical apparatus for marking a particular location in body tissue according to claim 15, wherein the clamp includes a screw movable from a first position which permits longitudinal movement of the elongated cable relative to the needle, to a second position which prevents longitudinal movement of the elongated cable relative to the needle.

17. A surgical apparatus according to claim 12, wherein the surgical apparatus further comprises an actuator housing and a deployment member operatively connected to the actuator housing to facilitate movement of the elongated marker from the retracted orientation to the deployed orientation.

18. A surgical apparatus according to claim 17, wherein the actuator housing includes at least one non-planar surface portion which interacts with the deployment member to retain the deployment member in at least one predetermined position.

19. A surgical apparatus for marking a particular location in body tissue, which comprises:

a housing defining a longitudinal passageway therethrough;

an elongated cable configured and dimensioned to pass through the longitudinal passageway;

a tissue marker operatively connected to a distal end of the elongated cable, the marker being selectively positionable in a retracted orientation disposed within the housing, an intermediate position wherein the marker is outside the housing spaced a distance from a distal end of the housing wherein the elongated cable is sufficiently rigid to maintain the relative orientation of the marker with respect to the housing independently of any support from the housing and a deployed orientation wherein the marker is rotated to a non-aligned relationship relative to a longitudinal axis of the housing; and an actuator assembly operatively associated with the tissue marker and movable between a first position and a second position to move the marker, the actuator assembly including a clamp operatively associated with the elongated cable to selectively prevent longitudinal movement of the elongated cable relative to the apparatus housing.

20. A surgical apparatus for marking a particular location in body tissue, according to claim 19, wherein the clamp is connected to the apparatus housing.

21. A surgical apparatus for marking a particular location in body tissue, according to claim 20, wherein the clamp includes a body portion defining a passageway therethrough to receive the elongated cable and a bias member movable from a released position, wherein the elongated cable is permitted to move longitudinally relative to the body portion and a clamped position, wherein the elongated cable is prevented from moving longitudinally relative to the body portion.

22. A surgical apparatus for marking a particular location in body tissue, according to claim 21, wherein the bias member is a screw threadably positioned in a bore formed in the body portion.

23. A surgical apparatus for marking a particular location in body tissue, which comprises:

a needle assembly including a housing and an elongated tube having a sharp distal end, the housing and elongated tube forming an longitudinal passageway therethrough;

a marker assembly including an elongated cable configured and dimensioned to pass through the longitudinal passageway and an elongated tissue marker attached adjacent a distal end of the elongated cable such that the elongated marker is movable between a retracted orientation and a deployed orientation, wherein the elongated cable is sufficiently rigid to maintain the elongated tissue marker in each of said retracted and deployed orientations independently of any support from the elongated tube; and an actuator assembly operatively associated with the elongated marker, wherein movement of the actuator assembly from a first position to a second position moves the elongated marker from the retracted position to the deployed position.

24. A surgical apparatus for marking a particular location in body tissue, which comprises:

a needle including a housing and an elongated tube having a sharp distal end, the housing and elongated tube forming a longitudinal passageway therethrough;

an elongated cable configured and dimensioned to pass through the longitudinal passageway and defining a central longitudinal axis;

an elongated tissue marker attached adjacent a distal end of the elongated cable and axially offset relative to the central longitudinal axis of the cable, the elongated marker being movable between a retracted orientation and a deployed orientation; and an actuator assembly operatively associated with the elongated marker, wherein movement of the actuator assembly from a first position to a second position moves the elongated marker from the retracted orientation to the deployed orientation such that the elongated tissue marker is disposed outside the tube wherein the elongated cable is sufficiently rigid to maintain the relative orientation of the marker with respect to the housing independently of any support from the housing.

25. A surgical apparatus for marking a particular location in body tissue, which comprises:

a needle including a housing and an elongated tube having a sharp distal end, the housing and elongated tube forming an longitudinal passageway therethrough;

an elongated cable configured and dimensioned to pass through the longitudinal passageway and defining a central longitudinal axis;

an elongated tissue marker attached adjacent a distal end of the elongated cable and being controllably movable from a retracted position, to an intermediate position and further controllably movable to a deployed position wherein the marker is reoriented with respect to a longitudinal axis of the elongated tube wherein the elongated cable is sufficiently rigid to maintain the relative orientation of the marker with respect to the housing independently of any support from the housing.

* * * * *